(12) United States Patent
Rilum et al.

(10) Patent No.: US 10,168,298 B2
(45) Date of Patent: Jan. 1, 2019

(54) ELECTRICALLY DETERMINING MESSAGES ON AN ELECTROPHORETIC DISPLAY

(71) Applicants: John Rilum, Tustin, CA (US); Paul Atkinson, Poway, CA (US)

(72) Inventors: John Rilum, Tustin, CA (US); Paul Atkinson, Poway, CA (US)

(73) Assignee: Chromera, Inc., Poway, CA (US)

( * ) Notice: Subject to any disclaimer, the term of this patent is extended or adjusted under 35 U.S.C. 154(b) by 0 days.

(21) Appl. No.: 15/392,132

(22) Filed: Dec. 28, 2016

(65) Prior Publication Data

US 2017/0292933 A1 Oct. 12, 2017

Related U.S. Application Data

(63) Continuation-in-part of application No. 14/927,098, filed on Oct. 29, 2015.

(60) Provisional application No. 62/408,905, filed on Oct. 17, 2016, provisional application No. 62/199,653, filed on Jul. 31, 2015.

(51) Int. Cl.
| | |
|---|---|
| *G01N 27/447* | (2006.01) |
| *G09G 3/00* | (2006.01) |
| *G06F 3/147* | (2006.01) |
| *G09G 3/16* | (2006.01) |
| *G09G 3/34* | (2006.01) |

(52) U.S. Cl.
CPC ....... *G01N 27/44769* (2013.01); *G06F 3/147* (2013.01); *G09G 3/006* (2013.01); *G09G 3/007* (2013.01); *G01N 27/4473* (2013.01); *G01N 27/44713* (2013.01); *G09G 3/16* (2013.01); *G09G 3/34* (2013.01); *G09G 3/344* (2013.01); *G09G 2380/04* (2013.01)

(58) Field of Classification Search
CPC ......... G01N 27/44713; G01N 27/4473; G01N 27/44769; G09G 3/007
USPC .......................................... 345/89, 207, 690
See application file for complete search history.

(56) References Cited

U.S. PATENT DOCUMENTS

| | | | | |
|---|---|---|---|---|
| 6,924,781 B1* | 8/2005 | Gelbman | ............... | G06F 3/1454 340/10.6 |
| 2001/0033678 A1* | 10/2001 | Hirai | ...................... | H04N 1/401 382/128 |
| 2003/0030612 A1* | 2/2003 | Yip | ...................... | G09G 3/3637 345/89 |
| 2003/0102858 A1* | 6/2003 | Jacobson | ............... | B41J 3/4076 324/537 |
| 2004/0086917 A1* | 5/2004 | Heller | .................. | B01J 19/0046 435/6.18 |
| 2004/0264734 A1* | 12/2004 | Wakao | .................. | G06T 1/0007 382/100 |

(Continued)

*Primary Examiner* — Tony O Davis

(57) ABSTRACT

Briefly, a method for verifying the visual perceptibility of a display is provided. An intended message is written to a bistable display. Pixels that comprise portions of the message are measured and evaluated to determine if the message actually displayed on the bistable display was perceptible by a human or a machine. In some cases, information regarding the message actually perceivable from the display may be stored for later use. Responsive to determining that a message is perceivable or not perceivable, alarms may be set, one or more third parties notified, or additional display features may be set.

37 Claims, 18 Drawing Sheets

(56) References Cited

U.S. PATENT DOCUMENTS

| | | | | |
|---|---|---|---|---|
| 2007/0058835 A1* | 3/2007 | Schrijen | ............ | H04N 1/32101 |
| | | | | 382/100 |
| 2009/0303259 A1* | 12/2009 | Shalom | ................ | G09G 3/3629 |
| | | | | 345/690 |
| 2011/0234557 A1* | 9/2011 | Yang | ...................... | G09G 3/344 |
| | | | | 345/207 |

\* cited by examiner

95 ↘

WRITE AN INTENDED MESSAGE TO A DISPLAY —— 96

DETECT STATE OF A SET OF PIXELS ON THE DISPLAY —— 97

EVALUATE STAE OF THE PIXELS —— 98
- first color
- second color
- ambiguous

DETERMINE WHAT PATTERN IS PERCEPTIBLE ON THE DISPLAY —— 99
- set alarm
- save
- associate with time

FIG 7A

100
Colors
FIG. 8
110
7 segment display
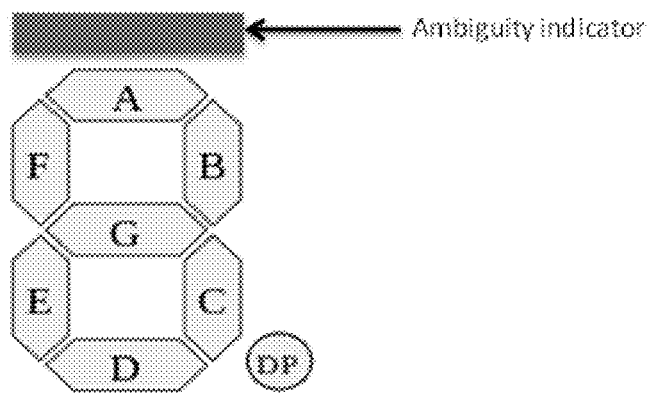
FIG. 9
120
Symbol Table
| A | B | C | D | E | F | G | Sym |
|---|---|---|---|---|---|---|-----|
| 1 | 1 | 1 | 0 | 0 | 0 | 0 | 7 |
| 1 | 1 | 1 | 1 | 1 | 1 | 1 | 8 |
| 1 | 1 | 1 | 0 | 0 | 1 | 1 | 9 |
| 1 | 1 | 0 | 0 | 1 | 1 | 0 | r |
...
FIG. 10

ELECTRICALLY DETERMINING MESSAGES ON AN ELECTROPHORETIC DISPLAY

RELATED APPLICATIONS

This application claims priority to U.S. provisional patent application No. 62/408,905, filed Oct. 17, 2016 and entitled "Electrically Determining Messages on an Electrophoretic Display," and is a Continuation-in-Part to U.S. application Ser. No. 14/927,098, filed Oct. 25, 2015 and entitled "Symbol Verification for an Intelligent Label Device," which claims priority to U.S. provisional patent application No. 62/199,653, filed Jul. 31, 2015 and entitled "Verification of Messages Displayed with Electro-Optic Devices," all of which are incorporated herein in their entirety. This application is related to U.S. patent application Ser. No. 14/479,055, filed Sep. 5, 2014, and entitled "An Intelligent Label Device and Method," which is incorporated herein in its entirety.

FIELD OF THE INVENTION

The present invention relates to an intelligent label that is particularly constructed to be associated with a good, and to enable trusted and verifiable reporting of the condition of that good. In one aspect, the label's electronics is used from time to time to interrogate its display and verify that the desired message is actually perceptible, and in some cases may be useful for generating a historical record of what was displayed or perceptible as the product moved through distribution and use.

BACKGROUND

Modern commerce is increasingly dependent on transporting goods using carriers as society embraces more and more online shopping. For example, modern consumers are increasingly using online shopping and common carriers for delivering wine, prescription medication, food, and sensitive electronic devices. To assist in tracking and monitoring the movement of sensitive and expensive goods, labels have been developed in the past that incorporate RFID communication and intelligence. In this way, at the point of shipment and throughout the major carriers, the good has the ability to be tracked. However, adoption of such RFID labels has been slow, as the equipment for initializing, loading, updating, and interrogating the label's RFID electronics is expensive, and typically only available at larger transfer points in the shipping transaction. Further, it is unlikely, and even rare, for the end consumer to be able to interact with the label. Since the consumer is a critical part of the delivery chain, and the consumer is excluded from participation in the information available on the label, the use of intelligent labels has been quite low and very ineffective in improving the customer experience.

Intelligent labels, packaging, tags, windshield stickers, stand-alone displays and other devices, collectively referred to herein as "intelligent labels," benefit from electro-optic devices that display messages that alert, update and inform the persons or machines proximate to them, as fully set forth in co-pending patent application Ser. No. 14/479,055, filed Sep. 5, 2014, and entitled "An Intelligent Label device and Method," which is incorporated herein in its entirety. This earlier application describes an intelligent label that can be attached to any good, and then is used to provide a visual indicator to a human or machine on some condition or event in that distribution path. Of particular interest therefore are bistable and permanently irreversible electro-optic displays and intelligent labels that comprise them. In one example of using the intelligent label, if a good is subjected to an extreme temperature or to vibration shock, then a visual indicator may be set such that a human or a machine will understand that the good is no longer of acceptable commercial quality. Of course, it will be appreciated that machines can perceive information outside of the normal human optical range. Messages for the intelligent label are visually perceptible forms of data, information, content, text, patterns, images, shapes, symbols, codes, and colors, for example. It is important to note that these are visual systems and the messages may change one or more times over the life of the intelligent label. Further the power source that drives them may be limited or intermittent or susceptible to accidental or intentional disruption. Other components of the intelligent label may also fail or be subject to tampering. In this way, the message that is intended by the local electronics to be displayed on the intelligent label may not actually be what the user or machine perceives. Accordingly, in some applications the utility and value of intelligent labels may depend on the confidence with which the messages can be relied upon to make decisions and take actions, and further, that the actual messages perceptible at the time those decisions were made or could or should have been made, and actions were taken or could or should have been taken can be reliably and securely verified.

In one example, doctors and other healthcare professionals need to know that they will only be held accountable for decisions made and actions taken based on the information reliably available at the time. Hospitals need to know too. As do patients and insurers and everyone else with a stake in the outcome. And they also need to know that if something goes wrong, the system cannot be tampered with and of its information is trustworthy. In a specific example, a bag of blood has reached its maximum allowed time out of refrigeration, and the electronic circuitry on its attached intelligent label has instructed a message to be displayed on the bag's irreversible display that indicates that the bag of blood can no longer be used safely. In this way, the electronic messages stored within the intelligent label's processor and memory would indicate that at the correct time the visual indicator transitioned to show that the condition of the blood had changed was no longer safe. However, in some cases an electronic or logical failure may have occurred and the visual alert message was never perceptible to the nurse or doctor. To correctly assess liability for wrongly using the blood, it would be important to know precisely what was visible on the intelligent display at the time the alert should have been set.

In another example, an experimental drug may have its expiration date shortened due to a better understanding of the drug's deterioration over time. In such a case, an intelligent label may be updated remotely to remove the original expiration date, and replace the date with a new, shorter expiration date. A patient may wrongly continue to use the drug after the new expiration date, and may later claim that the new expiration date was never displayed. Accordingly, it would be important to know what, if any, change had been made on the label at the time the expiration date should have been changed. Having such a historical understanding of what was actually displayed could be critical to patient care and assigning liability. More particularly, in some cases what was actually displayed may not have communicated the intended message to the patient or care giver. For example, even if the intended message was correct, a defect in the display or display electronics may have caused an error in what was actually displayed, and therefore may have failed to communicate the intended message. More broadly, this problem occurs any time a manufacturer, distributor, or person in control of a product wants to update the information displayed to the user or consumer. Accordingly, it would be highly desirable that an intelligent label be able to determine if the intended message was perceptibly displayed at a particular time, and in some cases generate and maintain historical record of what was actually displayed for later evaluation.

It will be appreciated that different applications require different levels of confidence in the verifiability of the system. Often it is not enough to rely on an inexpensive processor having issued a command, an on/off button being switched, or a signal being sent. Particularly over time, excessive heat or cold, shock or vibration, humidity, disruption to power, component fatigue/failure, read/write/refresh errors, electrical interference, tampering etc. can all impact the integrity of a visual system and thus confidence in the ability to verify what was actually displayed, and further what was actually perceptible, at a given moment in time. In other words, it often is not enough to know what was supposed to be displayed or what may have been displayed at a different moment in time.

Conventional displays (CRTs, LEDs, most LCDs etc.) can be thought of as self-erasing. That is, such a convention display is used to display an intended message to a user. However, there is no confirmation that the message has actually been presented in a way that is visually perceptible to the machine or human. For example, many internal and external factors can affect the visual perceptive ability of the display such as power disruption, excessive heat cold or humidity, shock vibration and pressures, and shorts and faults with the electronics or logic circuits. In some cases, feedback provided with in these conventional displays may indicate that the intended message has been displayed, however these internal or external events may limit or distort what has actually been displayed to, and perceptible by, the outside world.

Messages displayed by bistable (or multi-stable state) displays such electrophoretic and certain cholesteric or nematic LCDs are to varying degrees stable without the continuous application of power. By design, they are however reversible and the displayed messages are therefore subject to accidental or intentional erasure or alteration. The displayed information therefore cannot be verified reliably visually. As used herein the term visual refers to messages, images and the like that are perceptible by both humans and machine. Certain messages however may be perceptible by machine but not perceptible by humans. For example, they may reflect light at wavelengths outside the human perceptible range (of approximately 390 to 770 nanometers). This characteristic may be exploited in a number of ways, for example to create watermarks and other messages in response to events that are machine perceptible (readable) but not perceptible by humans. The verification systems and means described herein may be utilized with such non-visual, but machine perceptible messages.

In bistable electrophoretic displays, the application of an electrical field switches the position of charged ink particles creating two visible "states" corresponding to, for example, a white and black state as seen by the viewer. The ink particles are typically compartmentalized by use of microcapsules or microcups. Each microcapsule may contain a single or several types of ink particles, e.g. each corresponding to a specific color or optical characteristic, which may have varying degrees of mobility in the suspension fluid as a function of the applied electric switching field. The suspension fluid may further have a different optical characteristic to that of the ink particles, such as, clear, colored, absorbing, etc.

In U.S. Pat. No. 6,995,550 B2, electric sensing signals corresponding to the presence of a single type ink contained in microcapsules are discussed. In one mode discussed, a complex electrode pattern containing small detection gaps must be incorporated with the signal contribution primarily coming from the detection gaps that are positioned near the center of a microcapsule. As microcapsules are typically arranged in random patterns, only ink particles from a subset of microcapsules will contribute to the sensing signal. In another mode described, the presence of the ink particles (e.g. on the viewer side of the display microcapsules) are sensed by simply applying another write signal to the electrodes, and depending on the polarity of the write signal, deduce whether the ink particles were present or not. If the probing write signal is of the same polarity as the original write signal applied to set the display state, there will be no or only a small transient current present as all or most if the ink particles are already at or near one side of the display defining the presumed state. This scheme assumes that not only the state was presumed to be the correct one, but also that the display pixel/segment is functioning correctly. However, if the latter is not the case, for instance due to some irreversible damage present (for example, a discontinuity in of the two corresponding pixel electrodes, or an undesirable chemical degradation within the microcapsule), there could also be no, or only a small (residual), transient current irrespective of the state of the display pixel/segment. In order to electrically confirm the integrity of the display pixel/segment, the opposite polarity of the probing write signal could deliberately be applied. However, this method would thus change the very display state that is to be verified electrically.

Based on the above it becomes clear that it is desirable to have electrical verification methods and systems, which utilize the same set of electrodes employed for setting the display state, and in which substantial portion of ink particles from each microcapsule or microcup within a pixel or segment contribute to the verification signal. Furthermore, it is desirable to not disturb or only minimally disturb the optical display state during the electrical signal verification process to confirm the optical display state.

Accordingly, there is a need to reliably verify that an intended message has been presented on a display in a visually perceptive manner. In some cases, the stakeholders would also benefit from generating and maintaining a historical record of what was actually perceptibly displayed on the label.

SUMMARY OF THE INVENTION

An intended message is written to a display, which may be bistable. Pixels that comprise portions of the message are measured and evaluated to determine if the message actually displayed on the display was perceptible by a human or a machine. In some cases, information regarding the message actually displayed on the display may be stored for later use, irrespective of whether or not the display provided a perceptible message. Responsive to determining that a message is perceivable or not perceivable, alarms may be set, one or more third parties notified, or additional display features may be set.

In one example, the perceptibility of a message written to an intelligent label can be verified. More specifically, electronic circuitry within the intelligent label writes an intended message to a bistable display. Electrical characteristics of the pixels on the bistable display are measured, and a contrast and color profile may be generated. This profile represents the actual message that would have been perceivable by a human or a machine. This actual message can then be compared to the intended message, and a level of confidence that the proper message was presented can be generated. In this way, it can be verified that the proper message would have been perceivable by a user or human at a particular time, for example, when a severe environmental event occurred. Further, a historical record may be generated and maintained regarding the visual state of the bistable indicator at various times in the lifecycle for the product during use and distribution.

Advantageously, the verification process and label disclosed herein allows the visual information on the label to be confirmed and verified that a proper message was displayed and perceptible at a particular point in time. And further, independent of the intended message, the verification processes and labels allow for determination of the actual information displayed, its meaning and its perceptibility. In this way, liability can be more accurately assessed, and the trustworthiness of the entire distribution and use cycle is dramatically improved.

A system and method for electrically determining visible or perceptible messages on electronic displays is disclosed herein whereby an electrical signal is accessed within the display which has one or more characteristics that directly or indirectly correspond to the optical state of the display, or more specifically to the optical state of a display pixel or segment (hereinafter collectively referred to as the "display state" or "state of the display").

This approach has the advantage of simplicity and allowing for verification or determination of the display state under no or low ambient lighting conditions, e.g., when the display system is located inside a packaging box.

Of particular interest here are bistable or multistable reflective displays, in which the display state remains stable over a time period significantly longer than the switching time without the application of power to the display. The inventions described herein however can be extended to other types of displays including, but not limited to, transmissive, transreflective or emissive (e.g. back or front lit) configurations that may or may not be bistable or multistable. Of yet further particular interest are bistable reflective displays which are based on electrophoretic display layers, in which solid particles and a suspending fluid are held within a plurality of cavities.

BRIEF DESCRIPTION OF THE DRAWINGS

FIG. 7A is a flowchart of a process for verifying the perceptive ability of a message in accordance with the present invention.

FIG. 8 is diagram of segment colors in accordance with the present invention.

FIG. 9 is a diagram of a seven-segment display in accordance with the present invention.

FIG. 10 is a symbol table in accordance with the present invention.

DETAILED DESCRIPTION OF THE PREFERRED EMBODIMENT

Figure 1:
FIG. 1 is an illustration of the front side of an intelligent label made in accordance with the present invention.

The intelligent label may take many forms, such as a traditional style label for attachment to a discrete box or package, it may be integrally formed on a package such as a shipping container or mailer, or it may take the form of documentation that accompanies a shipped product. In other examples, the label may be integrated or applied on prepaid gift cards for example, or can be integrated into the good itself. Generally, the intelligent label is intended to enable a highly trusted, robust, and accurate way for safely and securely confirming or reporting a change in the condition of a good, for example, while a good is transported from a point of origin to a consumer or it is held in stock prior to use. Additionally, the intelligent label enables analytics and an understanding of the quality and handling of the good over time that is not available with prior systems. Further, the intelligent label provides accurate and timely information to various participants in the handling and use process, including the end user, without the need for sophisticated processing, communication, or interrogation systems. In this regard, the intelligent label has a simple electro-optical display (indicator) for visually presenting selected important information about the quality and handling of the good. A preferred option is an irreversible bistable indicator that cannot be turned back to its original state electronically, and thus is naturally resistant to tampering or accidental alteration. In some labels one may use both bistable and irreversible indicators corresponding to different indicator functions. It will be appreciated that in some constructions the electro-optic indicator can be constructed with electrochromic material or electrophoretic material.

Bistable indicators may be used to temporarily present a code or information. Bistability means that the display or the indicator changes from a first optical state to a second optical state by using a powering protocol, and remains in the second optical state without the application of additional power. However, this state (the second optical state) can be reversed to the first optical state by applying a different powering protocol and can also be maintained in that state without subsequent application of the power. The length of stability in a given optical state is dependent on the application requirement and a suitable electro-optical display/indicating system meeting that requirement can selected. In some applications optical state stability without the application of power, on the order of a few minutes may be acceptable, while in other cases this may extend to several days, months or years. Certain non-emissive electro-optical systems such as electrophoretic, liquid crystal and electrochromic systems can be tailored for various bistability requirements. Another desirable property of these indicators is their environmental durability (time, temperature, humidity (moisture), pressure and radiation (e.g., UV) in both activated and non-activated states so that it is obvious from visually observing the indicator its last state of activation (or inactivation). This environmental stability ensures that it would be difficult to mistake the conveyance of its intended optical state and also difficult to tamper with and also results in a permanence of indicated information.

Referring now to FIG. 1, one example of an intelligent label 10 is illustrated. It will be appreciated that the intelligent label may take many forms, however the form illustrated is a fairly typical label for attachment to a good destined for shipment using carriers or delivery companies. In other examples, the label may be integrated into mailers or other shipping containers, may be part of shipping documentation, or may be integrated with the packaging, product or good itself as in the case of a gift card. Referring again to FIG. 1, label 10 is intended for attachment to a good using an adhesive backing. As with a traditional paper label, intelligent label 10 has a print area 11 that may be used for identifying the intended receiver for the good. It will be appreciated that the print area may contain many other kinds of information, such as additional information regarding the attached good, invoice numbers, purchase order numbers, and additional information to assist the shipper. It will be appreciated that the print information may be placed in many different areas in human-readable or machine-readable form. For example, the print area may include barcode or other man or machine readable 12 to facilitate a more automated way to track process through the shipping chain. The intelligent label 10 also has embedded electronics that enable wireless communication to and from the intelligent label 10 electronics, not visible from the front of label 10, including a power source such as a battery, a processor, memory, and wireless communication, typically in the form of an RFID communication processor. It will be appreciated that these functions may be integrated onto a single electronic device, or may be discreetly implemented. Accordingly, besides the tracking information that may be acquired from the print area 11, additional tracking information may be stored and communicated using the electronic RFID areas. The intelligent label may also have an optional power harvester to charge the onboard power source such as a capacitor or a battery. The power harvester may produce electric energy from light (e.g., solar cell), RF energy, or due to motion and vibration that the label is subjected to.

Intelligent label 10 typically has an actuator, not illustrated from the front, that activates the electronics in the label just prior to the label being attached to the good. For example, the label may have adhesive backing, that when removed, enables the capture of the particular date and time when the label is being attached to the good. To enable this, the processor would operate in a very low power state to maintain its timer, and then when the adhesive is removed from the back of the label, a higher power mode would be enabled that allowed capture and storage of the current time and day. In this way, the label itself can accurately capture when it is attached to a good in-service. The good may then be placed into the shipping chain, where at each transfer information may be captured from the label using the barcode 12 or from the electronic RFID communications, and additional information may be stored in the RFID areas as well, provided such RFID equipment is available at shipping locations. Actuation, or initiation of the electronics also may be via a variety of means including a remote signal (e.g. RF, optical or electrical) a mechanical, electro-mechanical or electrical switch.

Intelligent label 10 also has an electro-optic display area 13 for providing immediate visual information regarding the quality of the product without the need for interrogating the RFID communication system. In one example, the processor in the intelligent label 10 contains rules as to how long the shipping process should take. In a more specific example, the label 10 could be applied to a box of flowers. The shipper-grower may require that the flowers be delivered within a two-day time span. As soon as the label is applied to the flowers, the timer starts and begins counting the elapsed time that the flowers have been in the shipping process. Initially, the intelligent product label may indicate the flowers as being fresh, but if the shipping time goes behind the limits set in the rules, the processor may cause the electro-optic device to indicate not to accept the flowers. Thus, at any point in the shipping process the receiver would be put on visual notification not to accept the flowers. This point could be at the end consumer point, or could be at any other point in the shipping chain. In one interesting alternative, there could be a period of time when the product is not as fresh as implicit in the buyer's initial order, but yet would be acceptable by most consumers, particularly at a reduced price. In this case, the intelligent label could be set up to inform the end-user to call customer service. Upon calling customer service, the customer may be offered a discount or other incentive to accept the flowers, acknowledging that they are nearing the end of their freshness state.

In a more specific example of the electro-optic display, the electrochromic display may have an informational block 15 for providing additional specific information. The information in informational block 15 may provide coded information dependent upon specific attributes of the shipping process, e.g. elapsed time, monitored conditions etc. Typically, the informational block 15 would be activated in order to give more specific information as to the broad information given in area 13. For example, the intelligent label 10 shows that the product associated with this label should not be accepted. If, for example, a consumer removes a package from their mailbox with the "do not accept" highlighted, the consumer typically will not have the equipment necessary to interrogate the label through its RFID communication channels. However, at the time the "do not accept" electrochromic indicator was set, the label also provided an electrochromic indication that provided the additional information as shown in information block 15. Accordingly, when the consumer calls customer support for the provider of the good, the consumer can visually read the code included in block 15 to the customer service representative, and that particular code can be associated with a specific time or event causing the good to go bad. In this way, customer service obtains significant information that is accurate and trustworthy as to where in the shipping chain the product was mishandled. By providing such information, the chances for fraud are decreased, and the opportunity for improved customer service is enabled.

Label Construction

It will be appreciated that the intelligent label may take many forms, but for convenience, the structure and function of the intelligent label will be described with reference to a discrete label having an adhesive backing for attachment to a mailing package or good. It will be understood that other constructions for the intelligent label are consistent with this disclosure, such as a label integrated with a package, integrated onto shipping packaging, or integrated into shipping documentation. It will also be appreciated that other constructions or possible consistent with this disclosure.

Print Information.

Figure 2:
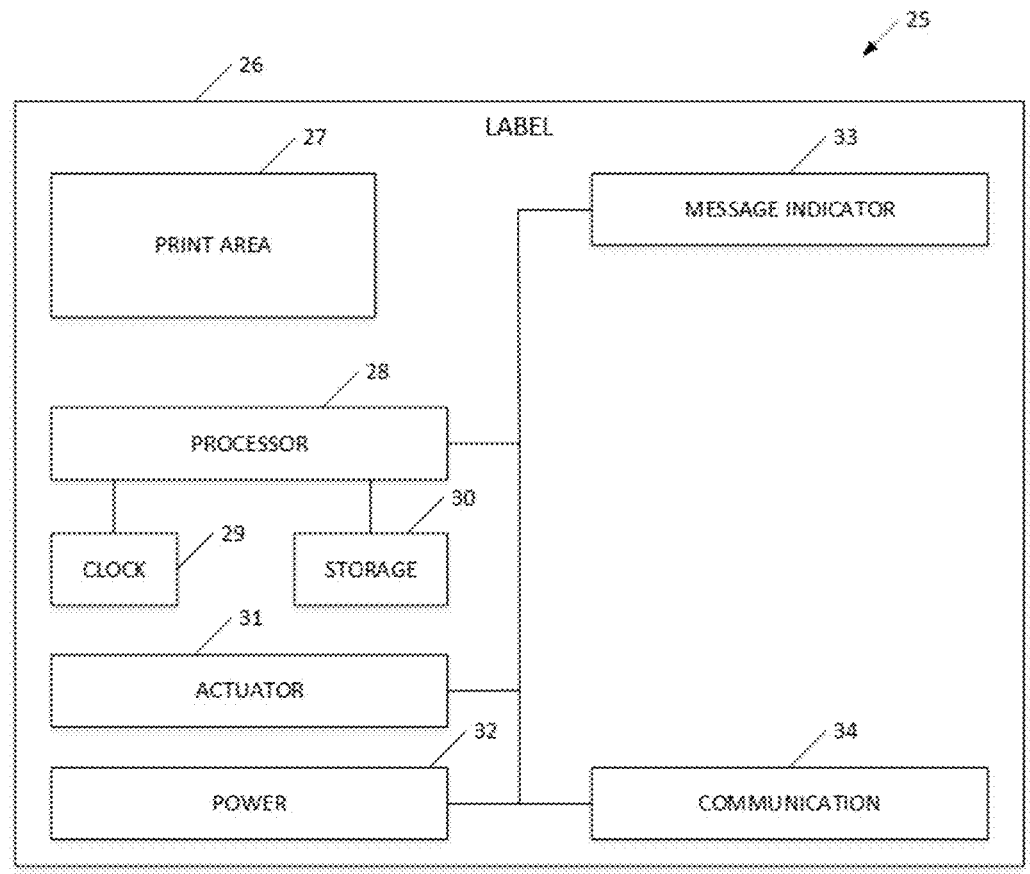
FIG. 2 is a block diagram of an intelligent label made in accordance with the present invention.

Referring now to FIG. 2, an example construction for an intelligent label 25 is illustrated. Intelligent label 25 typically has a front side, which has a print area 27 for communicating information regarding the good itself or the shipping and usage of that good. The information typically is printed onto the label using inkjet or laser printing processes, or may be preprinted. The print information may contain such information as name, address, invoice number, preferred shipper, and other traditional shipping information. Print information may also include information about the use of the goods, or rules regarding how the good should be stored or shipped. The print information may include textual information, as well as barcode or other types of machine readable formats. In this way, the print information can assist a human reading the information, and also may accommodate more automated data collection processes throughout the shipping chain.

Processor.

Intelligent label 25 also has electronics on or embedded within its structure. Electronics includes a processor 28 having an associated clock 29 and storage 30. The processor also manages communication using communication processor 34, which typically is an RFID radio. It will be appreciated that the various electronic components may be implemented using a single integrated circuit device, or may require multiple devices.

Power.

The electronics for intelligent label 25 require a power source 32 for operation, communication, and transitioning the electro-optic message indicator 33. This power may be supplied, for example, by a traditional primary or a secondary cell battery, a set of thin-film layers constructed as a battery, capacitor, or may be an antenna structure constructed to generate power responsive to an RFID field signal.

Message Indicator.

Also on the front side of the label, there will be an electro-optic message indicator 33, which in one construction may be an electrochromic or electrophoretic indicator, for providing additional information regarding the condition or quality of the good. The message indicator 33 may be bi-stable or permanent, i.e., irreversible. More particularly, the electro-optic material may be specifically formulated and activated in a way that it has two color or transparency states, with the electro-optic material remaining in the first state until it is activated to transition to the second state. Once electrically transitioned to the second state by the processor, this process is irreversible, and the message device 33 remains permanently in the second color or the second transparency state. The particular formulation of the electro-optic material is fully set forth in published US patent application number 20110096388, which is incorporated herein in its entirety.

In one example, message indicator 33 may be a first color while in the first state, and then when transitioned to the second state, visually present a second color. In another example, the electro-optic message indicator may change its transparency state. In this way, electro-optic message indicator 33 could be placed over printed information that would not be visible while the message indicator is in the first state, but then when transitioned, information below could be viewed through the now transparent message indicator. In another example, the message indicator 33 may be more complex and structured in a way that can build textual or numeric information, for example, such as using a segment or dot-based character construction. Further, although the message indicator 33 is described as having only two states, it will be appreciated that some indicators may have more than two stable states. In another variation, upon activation, the message indicator may transition from a first state to a second state irreversibly, and then upon further activation transition reversibly between the second and a third state, i.e., show bistability between the second and the third states.

In operation, electro-optic message indicator 33 would be transitioned according to rules set in the processor for the particular good that is being shipped. These rules would be implemented using processor 28, and when a rule is satisfied, the processor 28 would cause an appropriate electronic signal to transition the electro-optical material in the message indicator 33. For example, rules may be set that would cause the message indicator 33 to indicate whether or not the package was shipped and delivered within the allotted time.

In some cases, the electro-optic message indicator 33 may be structured as bistable electrophoretic indicator. Electrophoretic technology is most typically seen as an electronic paper display useful for handheld readers and small electronic displays. Electrophoretic technology is well known, but generally, an electrophoretic display forms images by rearranging charged pigment particles (pixels) with an applied electric field. Upon the application of an electrical signal, the pigments reorient themselves so that either a white side or a colored side is presented to the reader. By changing the electronic signal, the pigment can be oriented to the other visual state. Electronic paper, e-paper and electronic ink are display technologies that mimic the appearance of ink on paper. Unlike conventional backlit flat panel displays that emit light, electronic paper displays reflect light like paper. Many electronic paper technologies hold static text and images without electricity, but the display can be modified and changed upon a new application of power, or upon electronic or logic error. Although the intelligent labels are described generally using an electrochromic display, it will be understood that an electrophoretic display or a more general electro-optic display will work.

For example, it may be useful in some applications to use an electrochromic LCD display, that is, a display that is not typically considered to be either bi-stable or permanent. Even with such a display, it would be desirable to determine it, a particular time, the correct intended message was being displayed in a perceptible manner, and if not, to capture the pattern that was actually displayed. Herein, pattern is used broadly to include any arrangement of pixels, whether or not the pattern of pixels creates a human-recognizable symbol or character.

Communication.

Bidirectional communication may be provided with intelligent label 25 using the communication processor 34. The communication processor 34 may be an RFID radio, although other radios such as ZigBee, 802.11, or Bluetooth may be used. The communication processes on communication block 34 may be controlled by processor 28, with processor 28 managing what information is sent and received through the radio. Once information is received, it may be stored in storage 30, or rules may be applied to determine if action needs to be taken, such as setting the electro-optic message indicator 33.

Actuator.

Intelligent label 25 also has an actuator 31 for determining when the label is being attached to a good, for example. In this way, the actuator provides an accurate indicator of when the good is entering the shipping chain. The actuator in some cases may be provided as a physical mechanical device, and in other cases may be optical, electrical, electro-optical, RF, or chemical. It will be appreciated that the electronics can be activated at other trusted and confirmable times depending on the specific application. Actuator 31 can take many forms, depending upon the physical structure of the intelligent label 25. In one example, the actuator 31 is constructed along with the backing of the label, such as when the backing is removed to expose adhesive, the processor is provided with a signal that the label is about to be attached to the good. In this way, the processor can then store the accurate information regarding how the product entered the shipping chain, which can provide useful and accurate comparison information throughout the shipping process. In practice, the actuator can be implemented in many alternative ways. For example, the actuator may be set such that the removal of the label backing breaks an electronic circuit that can be detected by the processor. In another example, the removing of the backing material and placement of the label on the good may close a circuit, thereby giving a signal to the processor that the label has been attached to the good. In other examples, the actuator may be pressure activated through the application process, or provide an electronic signal that is generated by some physical action, such as by pulling a tab. It will be appreciated that actuator 31 maybe implement it in a wide variety of ways.

Sensor.

Figure 3:
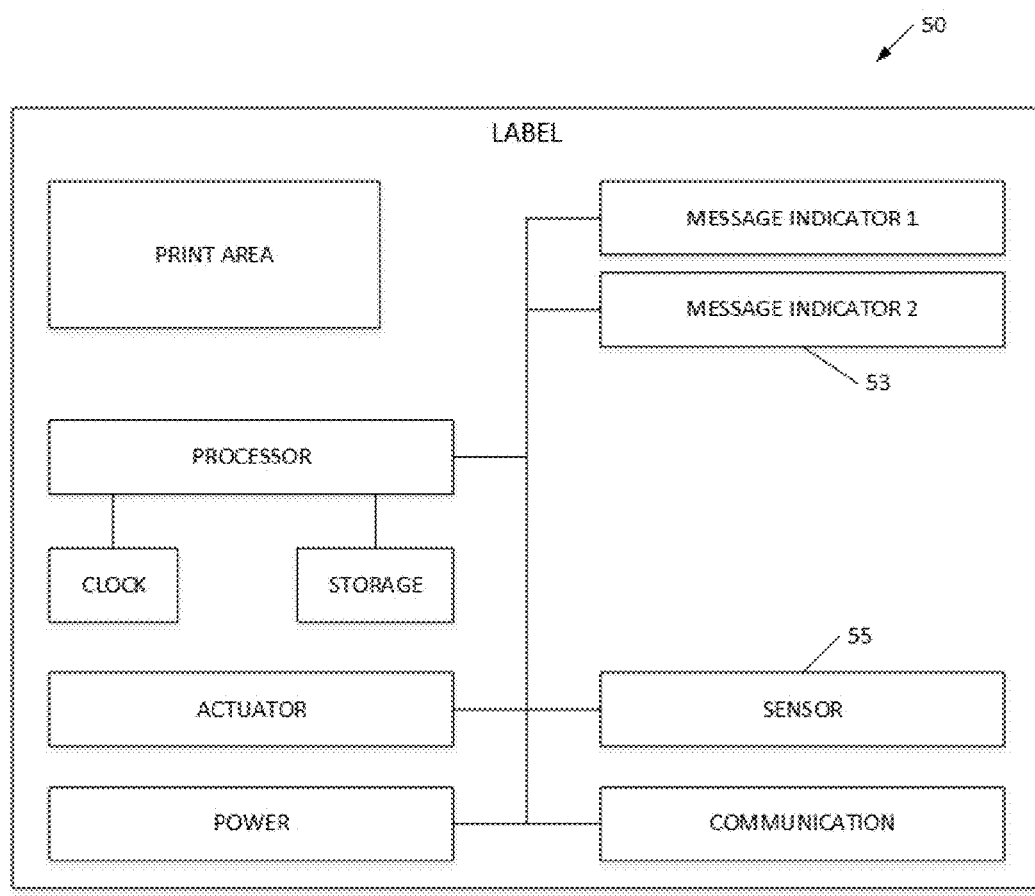
FIG. 3 is a block diagram of an intelligent label made in accordance with the present invention.

Referring now to FIG. 3, another example of an intelligent label 50 is illustrated. Intelligent label 50 is similar to intelligent label 25 described with reference to FIG. 2, so only the differences will be described. For example, intelligent label 50 includes a print area, processor, clock, storage, actuator, power, communication, and a first indicator as set out with reference to intelligent label 25. However, intelligent label 50 has a sensor 55 that is positioned on, in, or below the intelligent label 50 for sensing something about the environment that the good was subjected to during the shipping process. By way of example, sensor 55 could be a temperature sensor, a humidity sensor, and altitude sensor, a pressure sensor, an optical sensor, a vibration sensor (including a shock sensor), a humidity sensor, biological or a chemical sensor (including a gas sensor, a pH sensor), a magnetic sensor, and a smoke sensor, etc. It will be appreciated that a wide variety of sensors could be used depending upon the particular good being sold. It will also be appreciated that although only one sensor is shown on intelligent label 50, multiple sensors may be used. For example, a sensitive electronic device may be sensitive to vibration so a vibration sensor would be used, and may have parts that cannot be exposed to temperature extremes, so a temperature sensor would also be provided. However, for convenience intelligent label 50 will be described with reference to a single sensor 55.

The processor within intelligent label 50 will have a set of associated rules for the expected environmental conditions that the sensor 55 should be exposed to these rules can be set to simplistically monitor the sensor data, or may contain more sophisticated algorithms as to allowable conditions. For example, a good may remain in a quality state if exposed to a temperature for a short period of time, but would be considered out of specification if the temperature remained for more than a set period of time. It will be appreciated that a wide variety of rules may be set for sensor 55.

With the addition of one or more sensors, it is likely that the intelligent label 50 will need at least one more electro-optical message indicators 53. It will be appreciated that several electro-optical indicators and even of different types may be useful depending upon the number of sensors and sophistication of the rules for the good associated with intelligent label 50. In one example, an electro-optic indicator may be provided for visually indicating the letter, character, or code that provides more information regarding when or why the good was deemed to be unacceptable. Again, as the electro-optical indicator provides a human readable visual indicator, a person, such as the end consumer, would not need to wirelessly interact with the intelligent label 50 to obtain meaningful information regarding the state transition. In this way, a customer service representative interacting with the consumer would be able to not only verify that the consumer's product has been indicated to be a bad quality, it may be able to determine additional specific information that could improve the shipping process, and provide valuable information in satisfying the customer's needs.

State Verification.

Figure 4:
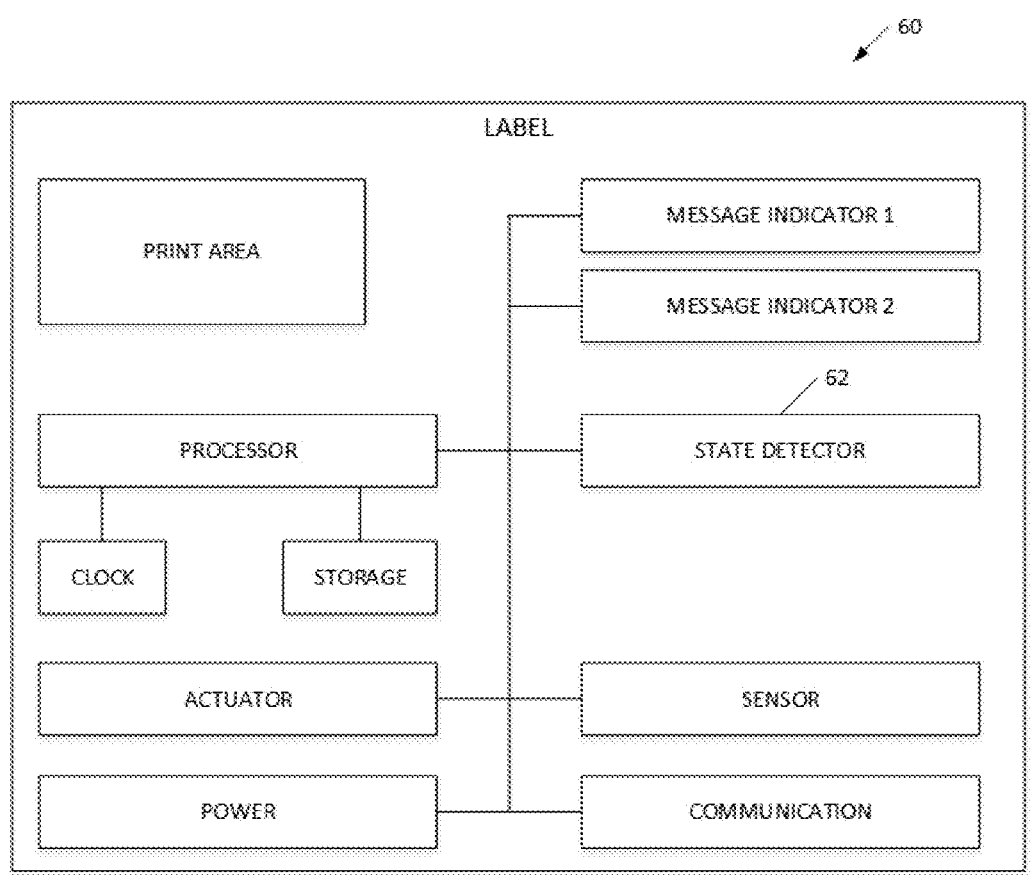
FIG. 4 is a block diagram of an intelligent label made in accordance with the present invention.

In some cases, particularly with high value goods, it may be desirable to add another layer of confidence that the electro-optic message indicator has properly transitioned to its second state. Referring now to FIG. 4, another example of an intelligent label 60 is illustrated. Intelligent label 60 is similar to intelligent label 50 described with reference to FIG. 3, so only the differences will be described. For example, as shown in FIG. 4, the state detector 62 may be connected to one or more of the electro-optic message indicators. In this way, when a particular rule is set to change one or more electro-optic message indicators, the processor will provide the required power signal to the electro-optic message indicator for it to change to its second state. After an appropriate period of time, the processor can then cause state detector 62 to confirm that the electro-optic material has changed states. This can be done, for example, using electrical measurements across the electro-optic indicator, or using optical sensors for physically detecting color, transparency, or opaqueness of the electrical material. In this way, the processor would not only track when it intended to set the electro-optic material into its second state, but would provide further verification information that the state was actually changed. The reliability of the state detection and confirmation may be further improved using knowledge of environmental conditions such as temperature, altitude, number of indicators, and their size, so that electrical parameters of the indicators are accurately predicted and tested both before and after activation.

Figure 5:
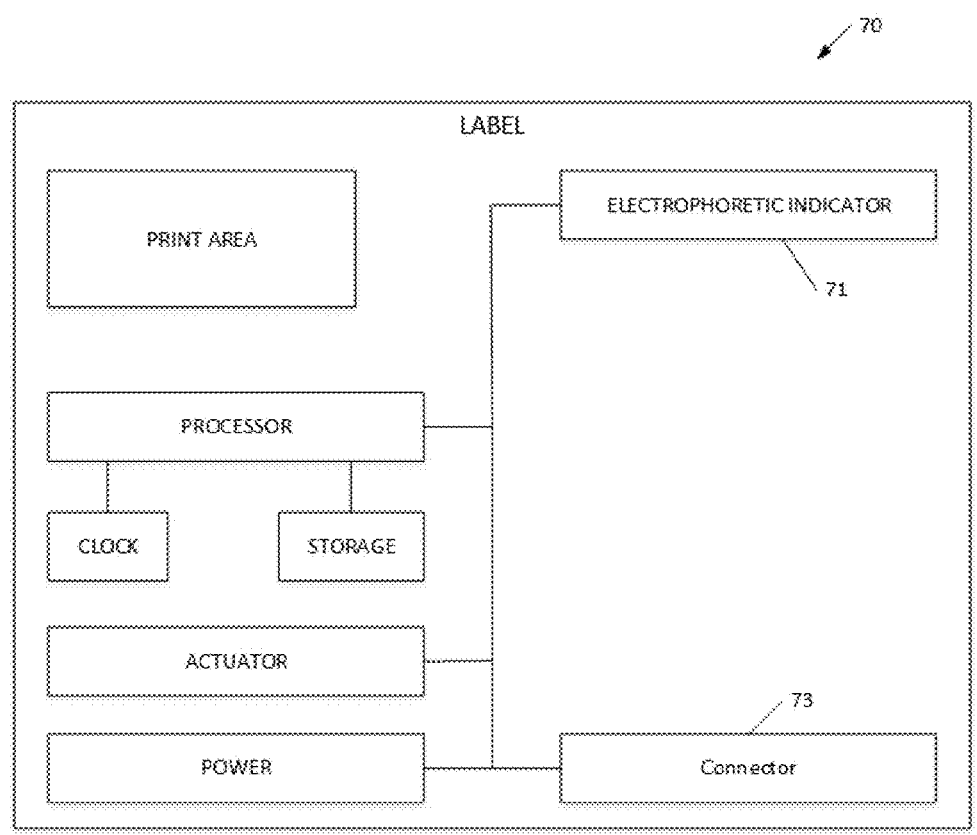
FIG. 5 is a block diagram of an intelligent label made in accordance with the present invention.

Referring now to FIG. 5, another example of the intelligent label 70 is illustrated. Intelligent label 70 is similar to intelligent labels 10, 25, 50 and 60 discussed with reference to FIGS. 1-4, so only the differences will be described.

Intelligent label 70 does not have a wireless communication capability, so is simpler and less expensive to manufacture, but still enables advantageous and trusted commercial transactions. Accordingly, label 70 communicates through a connector 73 to external or remote devices. Further, label 70 is illustrated having an electrophoretic indicator 71. It will be understood that the electrophoretic indicator 71 can be used with any of the electro-optic message indicators illustrated in FIGS. 1-4.

Message Verification

Pixels, as discussed herein, will be understood to be single addressable visual elements of the display. In some instances, a pixel may be a 'dot' and in others it maybe a shape such as a 'segment' used in the formation of a 'seven-segment' alphanumeric display. Pixels may also be a variety of shapes, symbols or images that are determined by the surface areas of the electrodes used to signal them. A shape of course may be comprised of multiple pixels. In many applications such as intelligent labels, the density, variety and resolution of the displayed messages is not typical of that required for consumer electronics. As such the messages may be generated using comparatively large pixels in shapes optimized for messages appropriate for the application instead of arrays of much larger numbers of significantly smaller pixels. Accordingly, a message consists of the visual 'state' of one or more pixels. In a monochrome display for example, a pixel typically has at least two intended states, on each of two high contrast colors (e.g. black and white) and depending on the display, a third (or more) state which is not one of the high contrast colors (e.g. gray or semi-transparent), but sits between the two high contrast colors. The perceptibility of a message or visual information further typically depends on the actual visual state of the message pixels and that of the pixels adjacent or proximate to them.

In certain electro-optic displays the visual state of a pixel corresponds to an electrically measurable characteristic of the pixel (e.g. voltage, resistance, capacitance, etc.). U.S. Pat. No. 6,995,550 B2 "Method and Apparatus for Determining Properties of an Electrophoretic Display" and referenced patents and applications describe such methods for electrophoretic displays. A pixel thus has a visual state and a corresponding electrical state. A pixel also may be considered to have a single 'state' that has both a visual and a corresponding electrical characteristic. The location or 'address' of each pixel relates to the electrodes used to set its state.

Described herein are systems and means for verifying that the messages actually displayed by bistable electro-optic displays are the same as those intended. That intended message may be determined for example by the output of the intelligent label's driver circuitry, by instructions/data in the intelligent label's processor/memory, or by monitoring signals transmitted to or received by the intelligent label. At a later time, this intended message can then be compared to the message that was actually perceptible on the display.

Verification of Perceptibility

Figure 6:
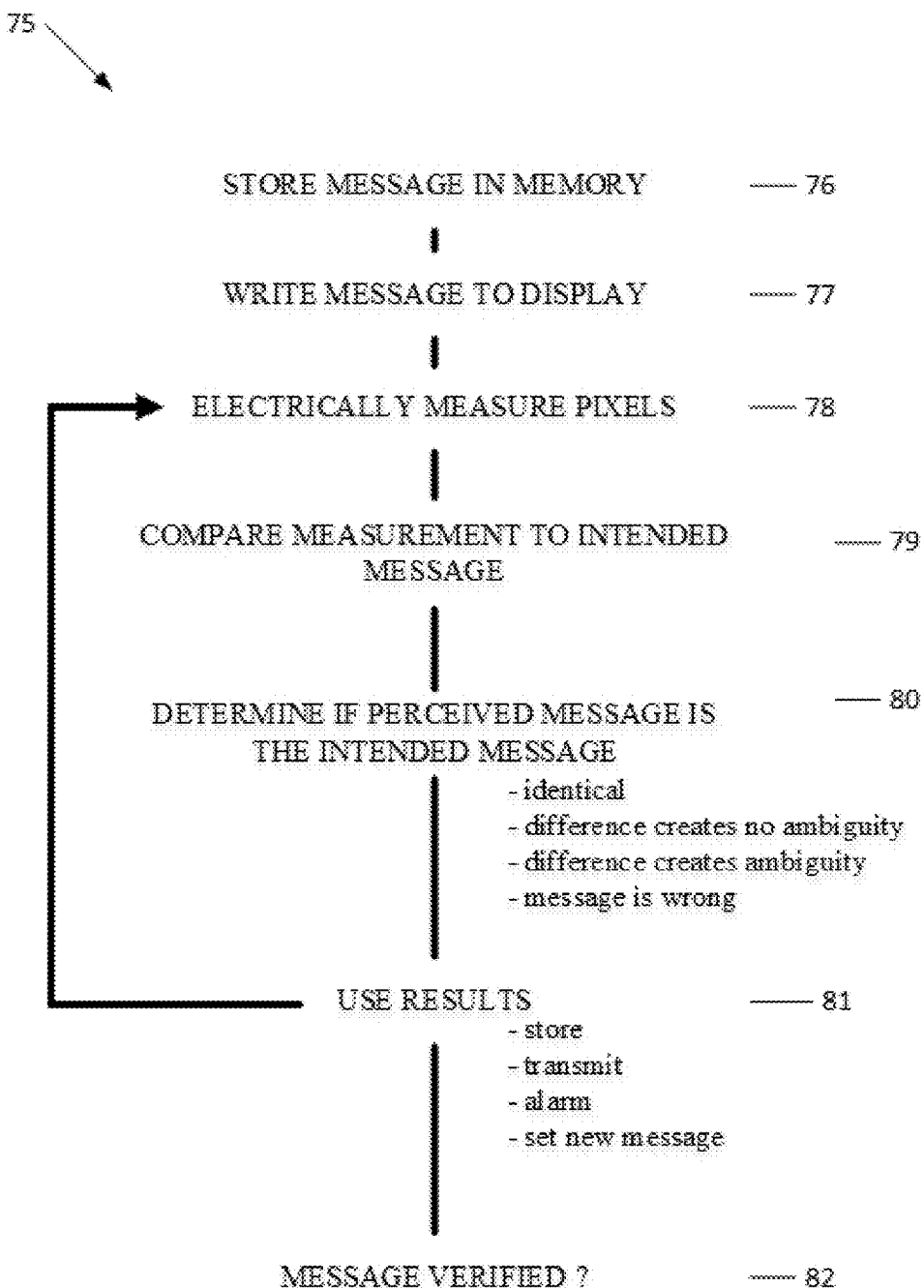
FIG. 6 is a flowchart of a process for verifying the perceptive ability of a message in accordance with the present invention.

Referring now to FIG. 6, a method 75 for verifying the perceptibility of a display is illustrated. It will be understood that the display may be bistable, permanent, or irreversible. In one example, the display may be part of an intelligent label, and in a particular construction may be employing an electrophoretic technology. In method 75, an intended message is typically generated by a computer processor or other electronic circuit, and is stored in a display memory as shown in block 76. It will be understood that such a message may be generated and stored in a wide variety of ways. In the example of an intelligent label, this message may be an expiration date, an indication of quality, or an alarm indicating that a particular environmental condition has been exceeded. It will be understood that the type and content of the message can vary greatly within the confines of the described invention.

Block 76 shows that the processor or driver circuitry attempts to write the intended message to the electro-optical display. In some cases, this intended message may be stored for later use in comparing to what was actually perceptibly displayed. It will also be understood that the intended message may be interrogated in various areas of the electronics, such as by evaluating contents of memory locations or evaluating driver circuitry. It will also be understood that method 75 may be used multiple times during the life of an intelligent label, since the intelligent label may have multiple messages that may be definable at various times in the distribution cycle. Method 75 may also be used to determine or confirm the continued perceptibility of the same message. Generally, the message comprises a set of pixels that when viewed together present the intended message. Depending upon the particular type of display technology used, these pixels may be white, black, gray, or set to another color. Typically, the pixels on the display will be activated using an electrode or electrode set to provide an electric stimulation or signal to each individual pixel. It will be understood that the process for activating pixels with electrodes is well understood.

At this point of method 75, the processor or electronic control circuitry has made an attempt to set an intended message onto the display. However, there is no feedback or verification that the intended message actually has been displayed. Accordingly, block 78 shows that the state of the pixels may be electronically measured to determine their visual state and the perceptibility of any message or information. That is, the individual pixels may be interrogated to determine if they are black, white, a particular color, or some state in between. Often, the interrogation of the pixels may be done using the same electrodes used to set the pixel, however in other cases other separate detection electrodes may be used. Also, it may not be necessary to evaluate or measure all of the message pixels. For example, there may only be a subset of the pixels that are required to perceptibly present the intended message. However, in many cases the simplest process is to use the same electrode used to set each pixel, measure the electrical characteristics of every pixel of the intended message, and store the measured electrical characteristics. It also may be advantageous to measure the electrical characteristics of the pixels adjacent to the message pixels or of reference pixels.

Each of the pixels can now be evaluated to determine if they are of the intended color and contrast. That is, it can be determined if the intended black pixel is actually black, or if it failed to transition at all, or if it is some level of gray in between. In this way, it can be understood if each pixel is properly set, and if not properly set, how close to the correct state it is. Accordingly, as shown in block 79, the intended pixel states corresponding to the intended message can be compared to the actual pixel states of the display.

In this way, it may be determined if the message visually perceptible to a user or machine is the intended message. For example, if all the pixels states are as intended, then the perceptible message is the intended message. If a few pixels are not fully set to their intended state, it may be determined that although not perfect, the intended message is still perceptible. In other cases, the differences between the intended states and the actual states may be so significant that it is determined that the message being displayed would not be perceptible by a user or machine. In making this determination, it may be useful to determine a subset of pixels that are actually necessary for generating a perceptible message. For example, a few pixels forming the base of a symbol may not have been properly set to a dark contrast, but having those few pixels properly operate is not necessary for a user to perceive and understand an intended message. That is, whether or not those pixels are black, white, or gray, their particular state creates little or no ambiguity in the perceptibility and understanding of the message.

With a level of confidence in the perceptibility determined, the perceptible information can be stored for later use, may be transmitted to a third-party, may set an alarm, or maybe used to set another new local message. For example, if method 75 determines that a new expiration date is not actually perceptible, the intelligent label may locally cause a second display to present a large red dot showing that there is a severe problem with quality. In a similar way, the label may cause an alarm or message to be sent to a third party, and an indication of the perceptibility of the expiration date as well as that of the red dot, may be stored for later use in verifying what message or information was actually available to user at a specific time. As illustrated by the arrow from block 81 to block 78, this verification process can be used multiple times to determine what was actually displayed at various times throughout the distribution and use cycle of the product. Finally, as shown in block 82, it can be determined if the proper message or messages have been perceptibly displayed for use by a human or machine throughout the product distribution and use cycle. In one application, the intelligent label has an indicator for informing a viewer that the message has an ambiguity. In this way, the user can take extra care in evaluating the message.

In applying method 75, it will be understood that algorithmic comparisons can compensate, adjust and account for errors in the measured results. Error correction techniques may also be applied. Confidence values/indexes may be generated/employed using the measured values, the importance of particular pixels to the perceptibility of the information, the accuracy of the perceptible information (and the benefits and risks of actions taken, or not, accordingly). In some instances, the comparison of measurements corresponding to the intended and measured information will be advantageously conducted off the label at the network level (e.g. to enable $3^{rd}$ party verification/auditing).

In one example of method 75, a bistable display uses a seven-segment display technology to present an alphanumeric character to a user or machine. The intended message, for example the number "7" is stored in memory. Three pixels (segments) out of the seven that characterize an alphanumeric character are 'addressed' by the appropriate electrodes (the top segment and the two vertical segments on the right). Signals are sent to color the three pixels with a first color (e.g. black). Independent of their last-known state the signals are preferably sent to each of the four other pixels comprising the seven-segment character to color them with a second color (e.g. white). Depending on their current state this may involve refreshing (re-writing) certain pixels' existing states. Optionally, signals may be sent only to pixels required to change state as determined by their last-known state or last-known-good state. If the state of the pixels proximate/adjacent (surrounding or interstitial to) to the seven pixels comprising the character can be electrically changed (e.g. the pixels are addressable) these pixels may also be sent signals to maximize the contrast between them and the message pixels and thus the perceptibility of the displayed information.

Using the same electrodes used to set the pixel's state, at least one electrical characteristic of each of pixel in the pixel-set appropriate to the intended message is measured. The pixel set in this example is preferably the seven pixels that make up the seven-segment display and the surrounding pixels. In another example, only the three segments that needed to be transitioned might be measured. However, greater confidence would be established if all seven segments were measured. But, in some power and time critical situations it may be advantageous to measure fewer than all the pixels.

The results of the electrical measurements are algorithmically compared to the previously stored intended message using predetermined measurable values corresponding to the different visual states possible for each pixel. The comparative results are stored in memory along with date/time and other device and event information as appropriate. If the result of the comparison is not as intended an error message/alarm is generated and wirelessly transmitted and optionally visually displayed (which itself might be subject to verification).

Figure 7:
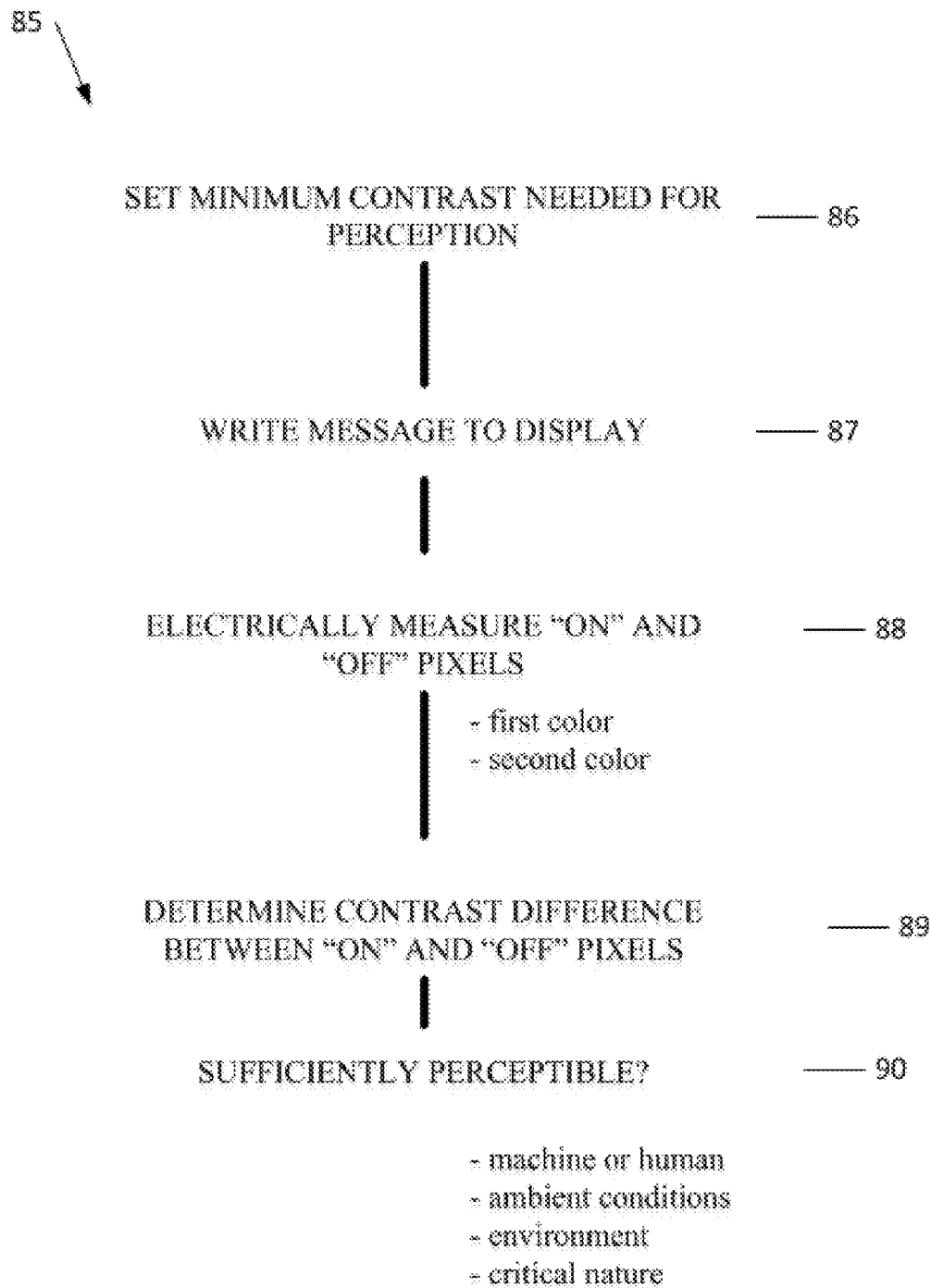
FIG. 7 is a flowchart of a process for verifying the perceptive ability of a message in accordance with the present invention.

Referring now to FIG. 7, a simplified version of method 75 is illustrated. Method 85 first sets a minimum contrast between the pixels states needed for perception of a message as shown in block 86. This minimum contrast may be set according to the particular operating environment and the likely sensitivity of the user. For example, some machines may have far greater sensitivity to changes and therefore require less contrast ratio as compared to human being. In another example, if the label or display is intended to be perceived in bright sunlight, an extremely high contrast ratio may be considered necessary. In block 87, the electronics in the intelligent label or the electronics associated with the bistable display write a message to the display. Thereafter, and preferably using the same electrodes that were used to write the message, electrical measurements are taken of the pixels to determine the state of those pixels. In this way, the "on" pixels may be measured to determine how dark or colored they are, and the "off" pixels can be measured to determine how light or non-colored they are. Accordingly, in block 89 the contrast levels may be compared between the on and off pixels. In this way, a display may be monitored for the effect of temperature, vibration, shock, electrical failure, material fatigue, damage or other conditions that could cause the contrast ratio of the display to diminish. Finally, in block 90, method 86 determines if the message is sufficiently perceptible for the particular application and particular environment. Again, in this step whether or not it is to be machine or human perception is important, and environmental and ambient conditions can be taken into consideration. Further, the more critical the messages, the higher level of contrast may be set.

Referring now to FIG. 7A, a method 95 for determining what is perceptible on a display is illustrated. As with methods 75 and 85 previously described, a message is written to the display as shown in block 96. However, significantly, method 95 is not concerned with verifying that the particular intended message was perceivably displayed. Instead, method 95 is focused and directed to determining, capturing, and creating a historical record of what was actually displayed and its perceptibility. Accordingly, block 97 then detects the state of the pixels on the display. In some cases, this could be all the pixels, and in other cases it may be a subset of pixels related to the intended message. Those pixels are evaluated as shown in block 98 to determine whether they are a first color, a second color, somewhere in between. Further, the types of messages that are displayable on the display may mean that some of the pixels are not crucial to any possible message on the display. In that case, whether or not a particular pixel is at its intended state is inconsequential to the actual message that could be perceived. That is, irrespective of the state of the pixel, it would create little or no ambiguity in the final message. Then, in block 99 it is determined what image or pattern is actually displayed. The actually displayed image or pattern can be saved, and may be associated with the date/time when the pixels were evaluated and associated information regarding its perceptibility. Depending on the image or pattern on the display, alarms can be set, additional display items set, or messages sent to third parties. It will be understood that other actions may be taken responsive to particular patterns.

As described above, it may be important to determine the visual content perceptible at a specific moment in time independently from its relationship to an intended message. The perceptible content may consist of a message that is different from the intended message, incorrect or misleading yet importantly it might be sensible given the circumstances. Or it might be completely devoid of meaning. The term content should be construed broadly to encompass whatever is actually displayed independent of its coherence or meaning.

Clinical research organizations and healthcare professionals for example, need to know that their decision to dispense a drug or infuse a patient with blood can and will be evaluated on the basis of the information available to them when the decision was made (not before or after). It may not be enough for an intelligent label to know that the information displayed wasn't correct. A user may not be able to tell the difference (it may 'look' correct/reasonable). For example, the difference between an expiration date, temperature reading or access code that ends in a zero or an eight or a four or a nine is a single pixel (segment). For better or worse a user may make a decision and take an action based on the immediately available information that may be erroneous. A single pixel (segment) can also be the difference between a plus and a minus sign or the international OK/Go and Warning/Stop symbols.

Measurements of the electrical state of the pixels in a pixel-set can be used in conjunction with appropriate reference tables or character recognition technique/systems to determine the content displayed and the messages it contains, if any. Measurements of the electrical state of the pixels in a pixel-set can be used to reconstruct the content actually displayed. That reconstruction in turn can be viewed, interpreted, analyzed, evaluated etc. by a person (or persons) or machine. And in conjunction with associated time/date information, an accurate, if not exact, reconstruction of the content displayed at a past moment in time could be used to judge whether or not a message was sufficiently perceptible and understandable to support a decision or action.

Measurements of the pixels' electrical characteristics can be taken at any time: before and immediately after updates, periodically over time, or in response to a command. Such measurements can be used to compare the original visual state with one or more past ones or absolute references to determine how they've changed over time or when the contrast in absolute terms or relative to each other pixels has unacceptably diminished. In the latter case the intelligent label could refresh the pixels or issue an alert.

These measurements can be taken and written to memory with numerical precision consistent with the accuracy of the measurement means and the pixel configuration (e.g. larger pixels are easier to measure), the number of pixels and number of measurements, and the power and memory available. The measurements can also be translated into a set of variables consistent with their visual states e.g. black, white or neither black nor white (e.g. gray, indeterminate, transparent, semi-transparent or opaque). These measurements can be compared over time to determine the stability/efficacy of the display and perceptible information (e.g. to environmental conditions, time). In this way, this process can be used to determine if the display in an intelligent label or other electronic device (e.g. consumer e-reader, tablet or phone, electronic shelf label or commercial display in a public venue) is fading or otherwise failing (or damaged, tampered with etc.) and can be used to predict failure or the need to refresh the appropriate pixels or take other action such as generating a warning or error message. As with the verification systems and means previously described, the systems and means used here can be to varying degrees local to the intelligent label or to a remote display.

In some instances, it is advantageous for an entity independent of the system owner or operator to be able to verify the presence, accuracy and perceptibility of messages at various moments in time, location or other conditions, especially when consumers are involved. For example, owner/operators of an electronic shelf label (ESL) system (or electronically updatable price tags) retailers (or their operators) have the ability to update prices and other messages consumers see when making purchase decisions. Retailers also have the ability to control the prices the consumer pays at check-out/the point-of-sale. At worst this this creates an opportunity for abuse/fraud. At best it creates uncertainty and doubt. Consumers, regulators and honest businesses have an interest in being able to simply and reliably verify the accuracy and consistency of the pricing messages actually used to make purchase decisions and payments.

This can be achieved by sending signals to the appropriate pixels in an ESL required to display the current price, immediately measuring the electrical characteristics of the appropriate pixels, and then algorithmically converting the measured results into displayed information (the displayed price) and storing the results along with the date/time and information that identifies the ESL or the SKU or other item identifier. Further, the process controls must be such that the measurements and storage of the displayed information (displayed price), date/time, ID etc. occurs every time signals are sent to alter the pixels. And preferably, new signals can't be sent until the displayed information is determined and stored.

The required process control can be accomplished in a number of ways. One way is to separate or isolating microprocessor functions such that the retailer for example can update the display, but cannot interfere with automatic measurement of the pixel's electrical characteristics immediately thereafter. Nor the storage of the results and the algorithmic conversion into displayed information. Nor would they be able to access that information or associate date/time ESL ID or product SKU etc.

As stated elsewhere the functions and process controls can be distributed advantageously. The microprocessor functions could be isolated, yet securely communicatively coupled as required within a single IC or split between two ICs. Control can partly be manifest over the driver circuitry because the update and monitoring functions would both preferably use the same electrodes.

The price charged for the item (SKU) at the POS and the time it was charged are typically printed on a receipt and electronically recorded/stored (with appropriate security, and preferably with a third party). Both the visual and electronic record (with proper security) can be electronically compared to the price displayed at the time (or most recently). This provides a secure framework for auditing pricing information or a 3rd party to act as a neutral monitor/trustee in regards to pricing (and other information).

In some implementations the intended messages would be advantageously displayed as composite images consisting of multiple pixels. A symbol (e.g. a 'dot') or icon, letter or number, for example could be comprised of multiple smaller pixels in the appropriate state (color) versus a single large pixel. To limit the complexity of the measurements, computations, and conserve available power, an acceptable level of verification of the displayed messages may be achieved by determining the pixel-set that makes up the intended message (or a component of the intended message), sending appropriate signals to the pixels in the pixel-set to produce the electrical state that corresponds to the desired message, and then measuring the aggregate electrical state of a set of pixels that comprise the intended message. That pixel set could be, for example, either all of the pixels that comprise the intended message, or in some cases a subset of the pixels that comprise the intended message. The process then algorithmically compares the measured results of the pixel-set with the corresponding previously determined pixels that comprise the intended message. It would be desirable that the algorithm compensates for 'noisy' data to compensate for activation (write) errors and measurement (read) errors.

Depending on the precision of the measurements, one or more pixels of the set of pixels that make up a large visual element e.g. a symbol, image (including a predetermined alphanumeric text string) may be measured and aggregated and used to represent the state of the visual element. Pixels may be sized according to the requirements (e.g. min size/shape).

The perceptibility of displayed messages, information, images and the like is directly related to the contrast between the pixels that make up the message. In other words, the ability to perceive a message depends on the contrast between a first, visual or colored state (e.g. white, or less than white) and a second, colored state (either black, or less than black) of the pixels. Note that the perceptibility of a message is not dependent on both, or either color being 'pure' (e.g. 100% black or 100% white) and the differential being 100% (it will always be somewhat less). What matters in most cases is that the differential in contrast (or contrast ratio) between the two states is sufficient for the message to be perceptible—not the absolute states in and of themselves.

A variety of algorithmic relationships may be utilized, but by way of illustration only, a display with an 80% 'white' first colored state can be thought of as also having a 20% black first colored state, and an 80% black second colored state may be thought of as having a 20% white second colored state. The differential in contrast between the two states would be 60%. The same would be true for a display with a 90% white first colored state and a 30% black second colored state.

If a 60% differential in contrast is sufficient for a message to be perceptible, then a message would be perceptible on either displays (80/20 and 90/30). A lower differential in contrast, e.g. 50% would indicate that perceptibility of the message was limited or impaired. The relative contrast of the two states is associated with a measureable characteristic. Thus a "contrast differential" can be used to verify or determine the visual state of a pixel or pixel-set and by extension the perceptibility a message. Note that optical states other than contrast, such as color, may also be used separately or in combination.

Another way of looking at contrast is to consider a contrast ratio. The human eye adjusts to the (average) light intensity in the image, by changing its pupil diameter (fairly quickly) and also light sensitivity of the retina (over several minutes). This is similar to a linear gain change in an (otherwise) linear photo detector. Simplistically, the eye sets the max intensity to the highest level of the pixels in the display (in practice average would be a better measure). Thus for the two cases: 80/20 would be normalized to 100/25, and 90/30 would be normalized to 100/33. It would therefore be easier for the eye to see the 100/25 (with a contrast ratio of 4:1), than the 100/33 (with a contrast ration of 3:1).

Note that if the charged/colored particles in electrophoretic displays are in other than their intended or "set" (bistable) state (either because they migrated from their set position or they're weren't adequately set to begin with) then they will be interspersed with other particles. This will have the effect of reducing both the optical contrast differential and the measurable electrical differential, relative to reference values.

A "contrast differential" as the term is used herein, is the difference between a first and second measurement of an electrical property of a pixel or pixel-set that corresponds to a first, visual ("colored") state and a second, colored state. The "contrast" of the colored states (perceptibility correlated to them, contrast differentials) being determined relative to each other subjectively (e.g. by human trials) and/or objectively (e.g. by measurement of light reflection, transmission, or absorption). Such determination can be made for each individual display (e.g. factory calibrated) or for each class of device, or other criteria.

In an example method all the pixels comprising the display are set to a first state where the pixels are colored to a first color (preferably the background color which is preferably white) and then a first measurement of an electrical characteristic is taken. The pixel or pixel-set that comprises the desired message is set to a second state where the pixel or pixel-set is colored to a second color that contrasts with the first color and a second measurement of the electrical characteristic is taken. Finally, the contrast differential is calculated between the two measurements. The calculated contrast differential then may be algorithmically compared to one or more previously generated reference "contrast differential," values, indexes or benchmarks).

Preferably, immediately prior to the first measurement, the pixel, pixel-set or all of the pixels comprising the display, is set to a first color, the first color being the background color (e.g. white). In the above example, all the pixels in the display were set to a first state, color and especially the background color (white). This has the effect of maximizing the contrast between the message pixel-set (the ones comprising the message and is this example, black) and the surrounding pixels (by setting them to white). A subset of all the pixels in the display, those that were known to surround the pixel set, could be used instead (and they could be set pre or post the setting of the pixel-set to the send color (black). And although less reliable, only the pixels surrounding the pixel-set that were last known (measured) to be of set of the second color could be used set to the first color, pre or post the coloring of the pixel-set.

In some cases, the contrast differential is determined without setting or resetting the states of the pixels in the pixel-set. For example, to compare it to a previous contrast differential and determine if the message has been stable over the interim interval or the display's efficacy has been impaired. The first color may be either dark (e.g. black) or light (e.g. white) and can be of colors other than black or white. The relationship between the electrical characteristic and the perceptibility of the message may be linear or nonlinear. Previously generated reference contrast differentials may be generated during the manufacturing process and supplemented by an optical verification system. Or, they may be generated at one or more times during the display's (and intelligent label's) life. As previously described, conditional rules/logic may be applied and actions taken in response to comparisons between contrast differentials.

As noted previously, the relationship between the optical state of a pixel and the corresponding electrically measured characteristic is required (e.g. for a given voltage or capacitance, there is a corresponding optical state). This information may be obtained by calibrating the electro-optic displays using automated means consisting of electrical measurements of the electrical state of pixels of different sizes, surface areas, shapes, volumes, thicknesses, masses, manufacturing defects and tolerances, etc. and optical measures of the displayed information. Further, the information may be calibrated to compensate for different environmental conditions (e.g. temperature, pressure, or humidity).

In certain instances, it may be advantageous for an intelligent label to create a verifiable visual alert/alarm based on the displayed message. And further, that the visual alert/alarm is, unlike that produced by a reversible bistable electro-optic device, irreversible permanent or near permanent (like a photograph). For example, if the displayed message was not as intended, a red dot or other symbol or message could be displayed to visually, and verifiably alert the user that the message displayed by the bistable electro-optic device was either incorrect or potentially inaccurate. Of interest therefore is an intelligent label comprising a bistable display and a permanently irreversible display. In a preferred embodiment, the intelligent label comprises an integrated electro-optic display comprising a bistable electrophoretic layer and a permanently irreversible electrochromic layer (such as that described in patent application US20110096388A1 "Flexible and Printable Electro-optic Devices) and common electrodes. And further, that the reversible electrophoretic and irreversible electrochromic layers utilize the same electrode layers.

Given the relatively small values for the measured electrical characteristics of electrophoretic pixels, it may be advantageous to include in the display or intelligent label means to minimize or compensate for electrical noise in the measurement system. Electrical noise is inherent in any electronic system design and is normally a strong design consideration. Electrical noise is generated both internally from switching digital logic, as well as from external sources, e.g. nearby electrical components, RF sources, etc. that are coupled into the system through internal wiring or signal traces, antennas, etc. Noise may be mitigated through design techniques, e.g. ground planes, layout and filtering so that it is typically well below those of the activation signals.

In the case of electrophoretic displays the noise is typically well below that of the signals that switch the display elements. It may however be on par with electrical measurements of pixels intended to determine their state. In such cases, in addition to executing good ground plane and signal routing designs, the display and associated electronics may take advantage of common-mode techniques (e.g common-mode noise rejection techniques) so that the measurements "ride" on top of the noise to the extent feasible. Additionally, they may use averaging of multiple measurements and comparisons to average reference levels to determine a difference between measured and reference levels. Other signal processing techniques may also be used optimize the detection and measurement of pixels.

FIGS. 8-18, discussed below, show an example implementation for determining perceptibility for a bistable display. It will be understood that there are many methods and processes that can be used, and this represents just one of the ways to detect and report perceptibility.

FIG. 8 provides an overview diagram of the color codes used in a representative implementation. In certain electro-optic displays the visual state of a pixel corresponds to an electrically measurable characteristic of the pixel (e.g. voltage, resistance, capacitance etc.). In an exemplary display these electrically measurable characteristics are divided into three ranges. One part of the range is mapped to one display color and another part of the range corresponds to a second color. Measurements that are between these range values correspond to an ambiguous reading. For displays that can support multiple colors, the set of values can be divided into additional ranges that can be associated with additional colors. Measurement ranges can be separated enough reliably to identify color sets. These values can be read to ascertain the current display value and established to set the appropriate color value for a segment on the display.

FIG. 9 corresponds to a commonly used seven-segment display. In one example, the typical seven-segment display is supplemented with a new ambiguity indicator, which can be set to display whether or not the seven segments are confidently displaying an intended message. Each of the seven letter-coded segments can be individually addressed and set or read through the electrical characteristic used in the design. In an exemplary case, the segments can take one of two colors. In order to communicate with the user of the display that the display reading for a particular character is ambiguous, a separate indicator can be used. This indicator can be set in the case that the read value of a segment within a character is ambiguous. Alternatively, a single ambiguity indicator can be associated with an entire message. Further, as described earlier, or messages and alarms may be generated and communicated. It will be understood that the inverse can be also be created: a "certainty" or "confidence" measure, index and indicator etc.

FIG. 10 corresponds to a symbol table for a seven-segment display that maps segment color values to symbols. Here, the allowable symbols are 7, 8, 9, and r. These symbols are the intended result of color patterns on the seven-segment display. For example, in this table for a two color display a 1 indicates "black" and a 0 indicates the color "white." The first row in the table corresponds to segments A, B and C being colored black and the other segments being colored white, or, depending on the display characteristics, uncolored. Such a pattern would generate a 7. If all segments are colored, as in the second row, then an 8 should be set on the display.

Figure 11:
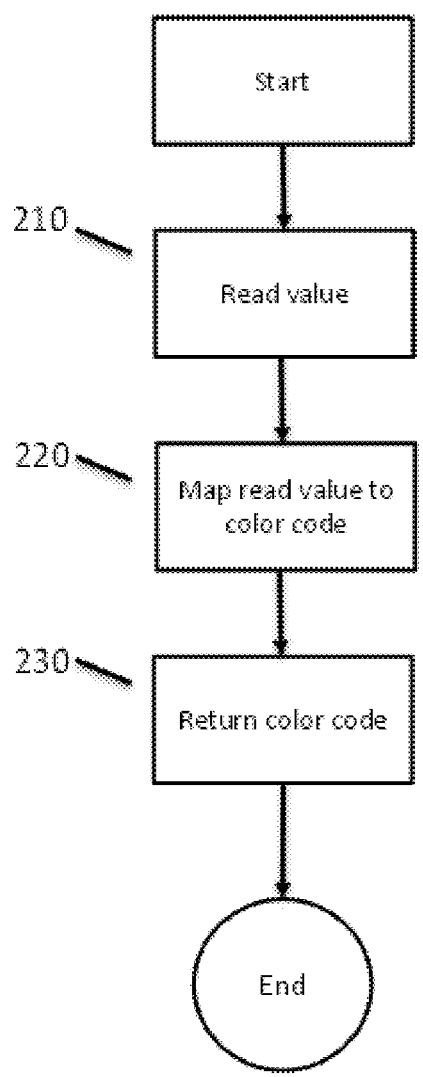
FIG. 11 is a flow chart of the segment color identification process in accordance with the present invention.

Process 200, Identify Segment Color, is diagramed in FIG. 11. Process 200 begins in process step 210 where the physical value of a single pixel segment (e.g. voltage, resistance, capacitance etc.) is assessed. Process 200 then proceeds to process step 220. This step maps the value read in process step 210 to the range values described above. In the case of the two color code display, this might be represented as "0", "1", or "2" for example. In process step 230 the result of this mapping is returned from the process. Process 200 then ends as to that segment, but can be repeated until all the required segments (pixels) are read and a color determined.

Figure 12:
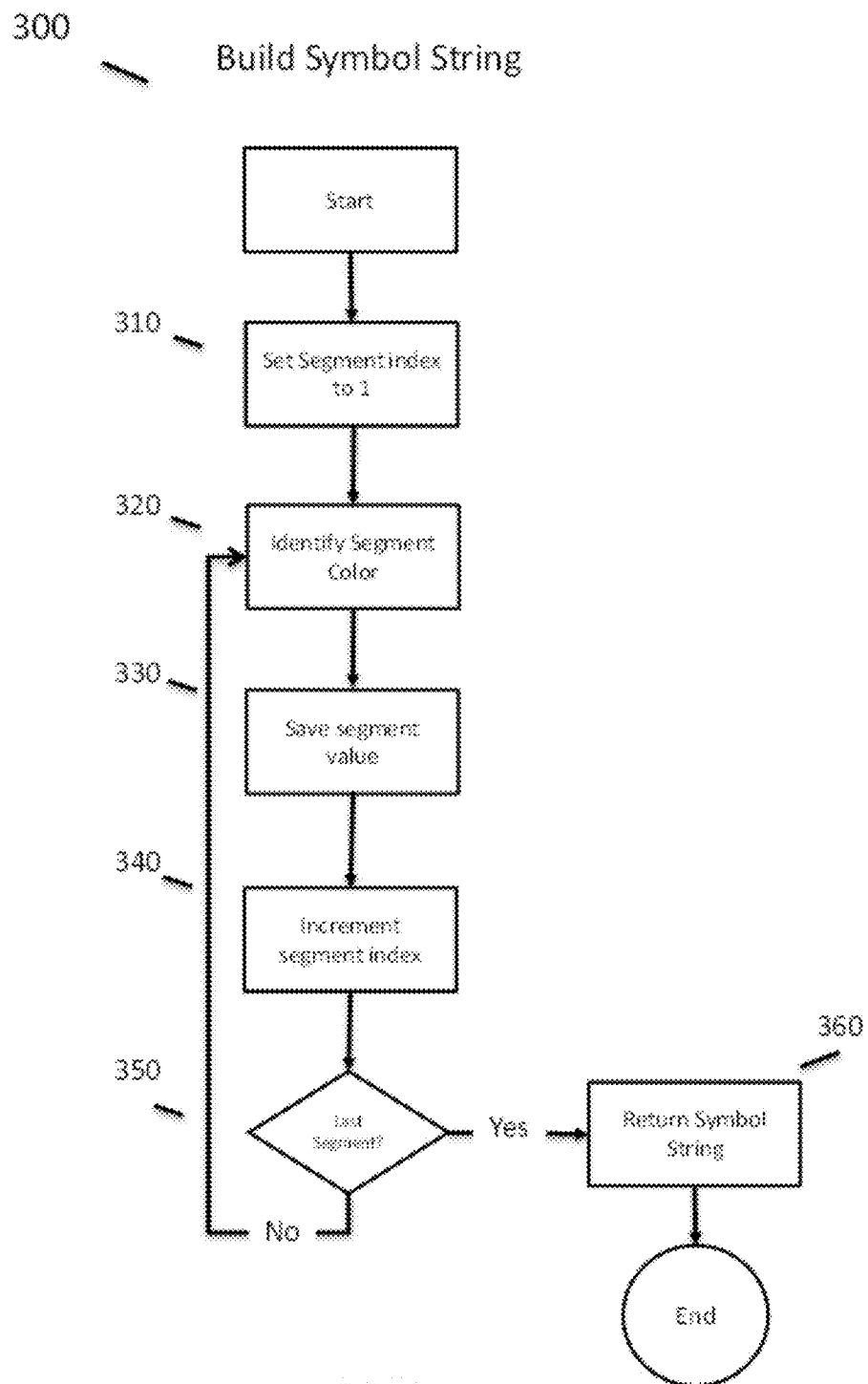
FIG. 12 is a flow chart of the symbol identification process in accordance with the present invention.

Process 300, Build Symbol String, is diagrammed in FIG. 12. This process compiles a collection of segment values into a symbol string. Process 300 begins in process step 310 where an index is set. Process step 320 invokes process 200, Identify Segment Color for the identified segment. The returned segment color is saved in process step 330. The segment index is incremented in process step 340. Process 300 then continues to process step 350, where it is determined whether this is the final segment of the display. If it is not, process 300 continues to process step 320. If this was the last segment, process 300 proceeds to process step 360 where the symbol string is returned. This symbol string represents the actual state of the segments as detected, and may include all the segments, or a subset of the segments. Process 300 then ends.

Figure 13:
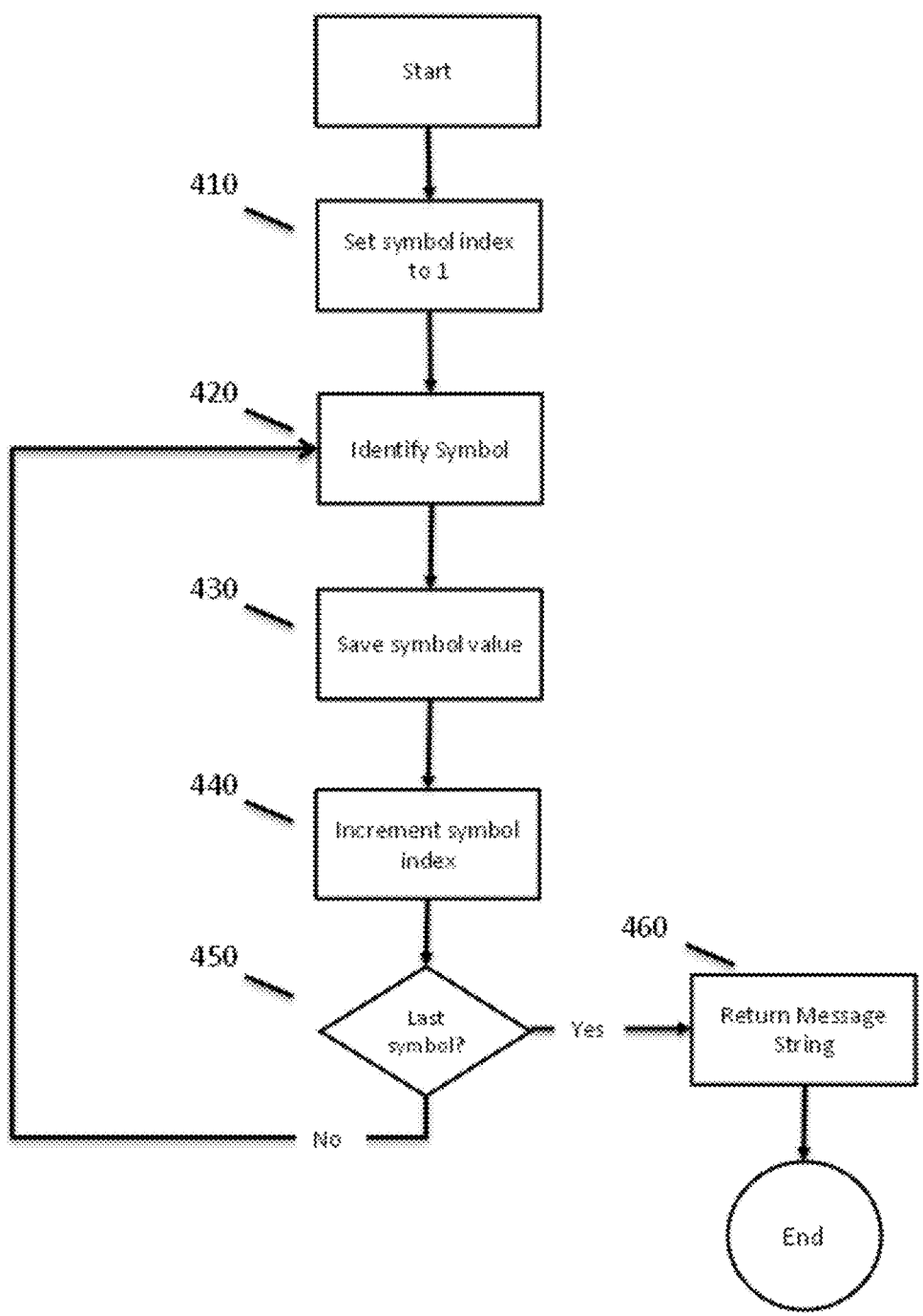
FIG. 13 is a flow chart of the message identification process in accordance with the present invention.

Process 400, Build Message String, is diagrammed in FIG. 13. Process 400 begins in process step 410 where an index is set. This process is useful for messages that comprise multiple symbols. Process 400 then proceeds to process step 420 where Process 300, Build Symbol String, is invoked. Process 400 then continues to process step 430 where the symbol string identified is saved. In process step 440 the symbol index is incremented. Process 400 then tests whether this was the last symbol to be processed in process step 450. If this was not the last symbol, process 400 continues to process step 420. If it was the last symbol to be processed, process 400 proceeds to process step 460 where the message string, the set of symbols identified, is returned. Process 400 then ends.

Figure 14:
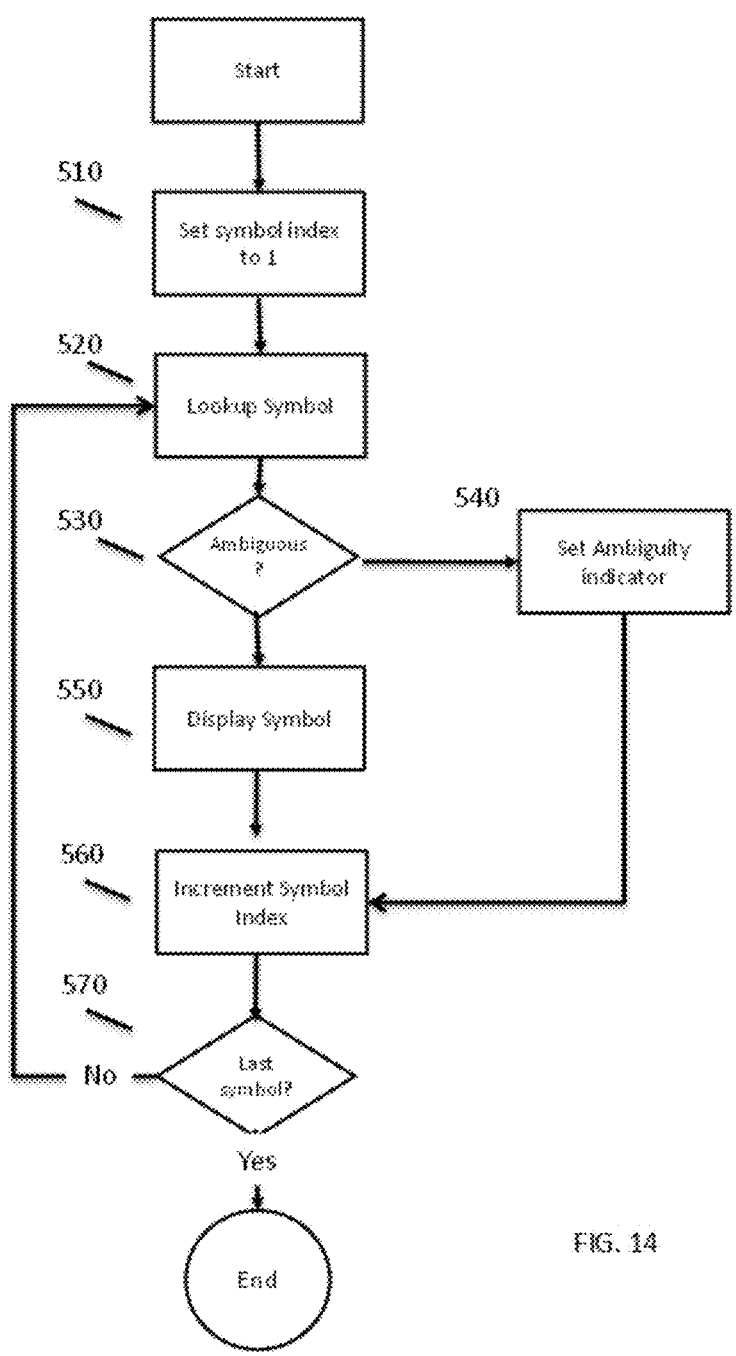
FIG. 14 is a flow chart of the message display process in accordance with the present invention.

Process 500, Display Message, is diagrammed in FIG. 14. Process 500 begins in process step 510 where the symbol index is set to 1. Process 500 the proceeds to process step 520 where process 600 (FIG. 15), Lookup Symbol, is performed. Process 500, then proceeds to process step 530, where it is determined whether the result of Process 600 was ambiguous. If it was not, process 500 proceeds to process step 550, where the symbol is displayed. If it was, process 500 proceeds to process step 540 where the ambiguity display indicator is set. As indicated in the description of FIG. 9, depending on the display, the may be one indicator per symbol, one indicator per display or another configuration that allows for appropriate communication. Process 500 then continues to process step 560, where the symbol index is incremented. Process 500 then proceeds to process step 570 where it tests to determine whether this was the last symbol to process. If it was not, process 500 continues to process step 520. If it was, process 500 terminates. If will be appreciated that ambiguity as to a particular segment, or even a particular symbol, may not result in an ambiguity to the overall message.

Figure 15:
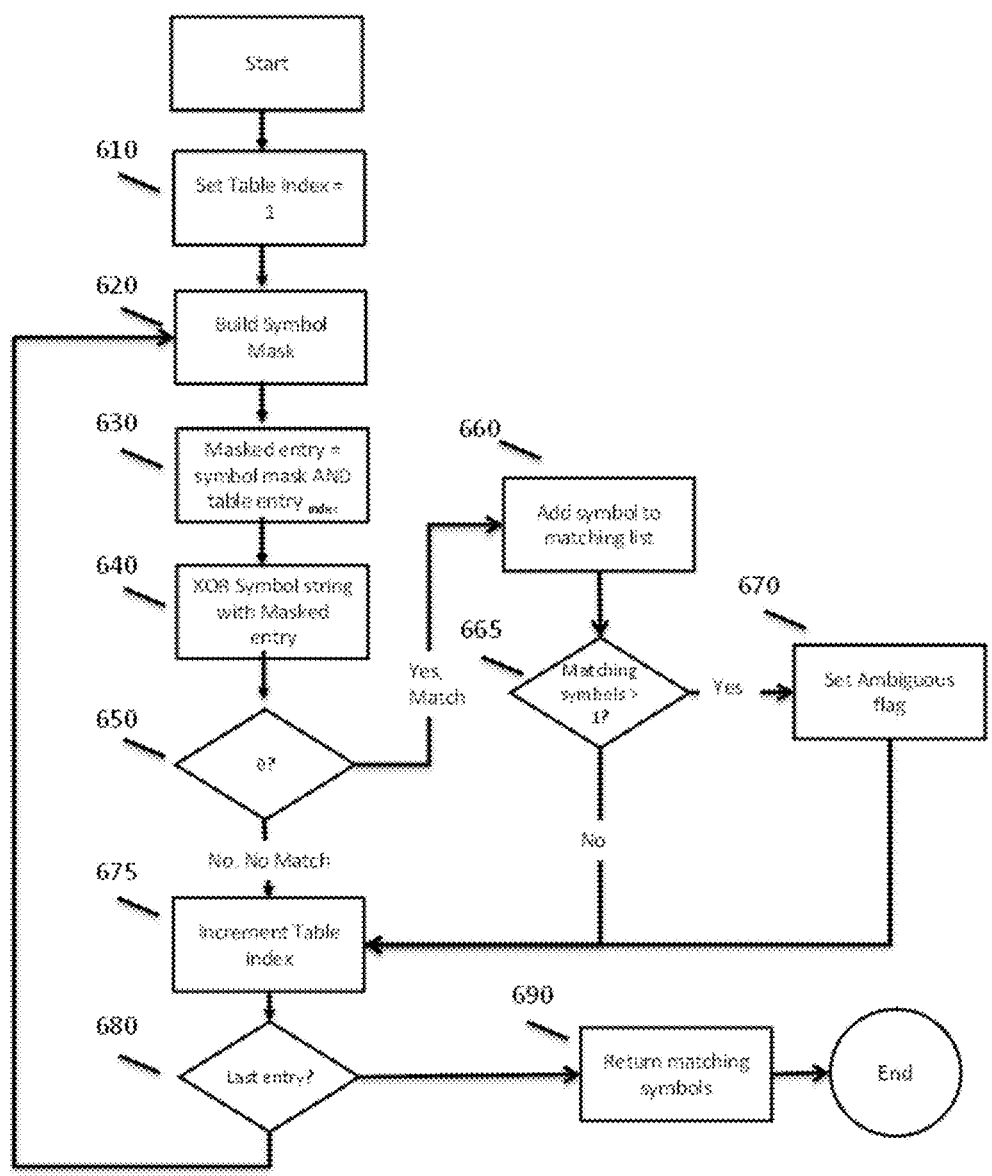
FIG. 15 is a flow chart of the symbol lookup process in accordance with the present invention.

Process 600, Lookup Symbol, is diagrammed in FIG. 15. Process 600 takes as input a symbol string. Process 600 begins in process step 610 where a table index is set to 1. The table index is used to iterate over the Symbol Table. Process 600 then proceeds to process step 620 where process 700 (FIG. 16), Build Symbol Mask, is invoked with the current symbol string. The result of Process 700 (FIG. 16) is a bit string mask. This mask has a zero in those symbol positions that are ambiguous. Process 600 then proceeds to process step 630 where the symbol mask is logically ANDed with the symbol table entry to create a masked table entry. The result of process step 630 is then logically XORed with the symbol string. This bit string will be zero if the table entry matches the symbol string for all non-ambiguous bits. Process 600 then proceeds to process step 650 where this bit string is tested. If it is not zero, this table entry is not a match for the symbol string and Process 600 proceeds to process step 675 where the table index is incremented.

If the test in process step 650 was true, the symbol string was a match and Process 60 proceeds to process step 660. Where the table symbol is added to the Matching Symbol List. Process 600 then proceeds to process step 665 where the length of the Matching Symbol List is tested. If the length is greater than 1, that is, there has been more than one match for the symbol string identified, Process 600 proceeds to process step 670 where an ambiguity indicator for the symbol string is set. Process 600 then proceeds to process step 675. In process step 665, if the number of matching symbols is 1, process 600 proceeds to process step 675.

Process 600 then proceeds to process step 680 where the table index is compared to the length of the symbol table to determine whether this was the last table entry. If it is not, Process 600 proceeds to process step 620. If it is the last entry, Process 600 proceeds to process step 690 where the symbols from the table that matched the symbol string are returned. Process 600 then ends.

Figure 16:
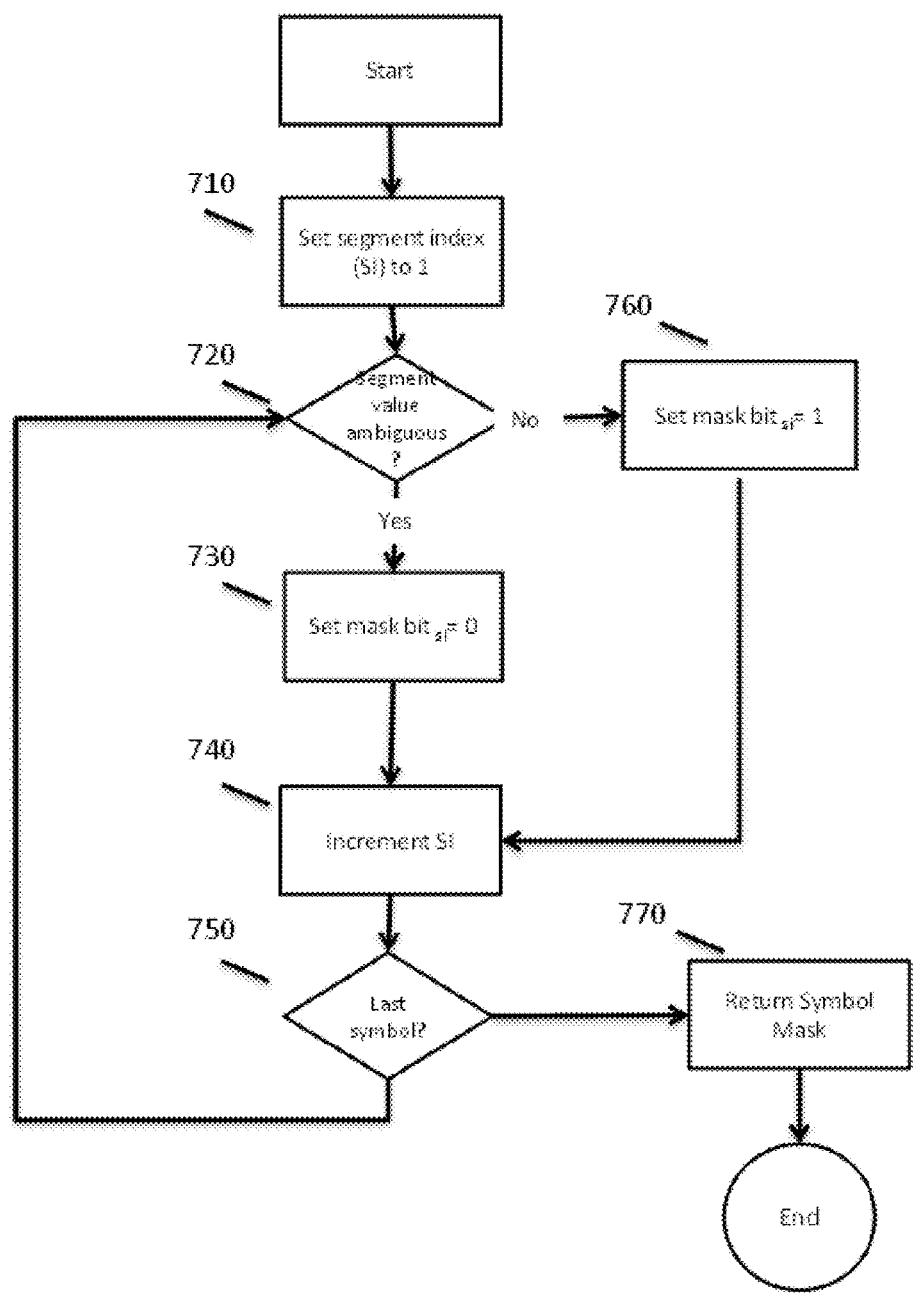
FIG. 16 is a flow chart of the symbol mask building process in accordance with the present invention.
Figure 17:
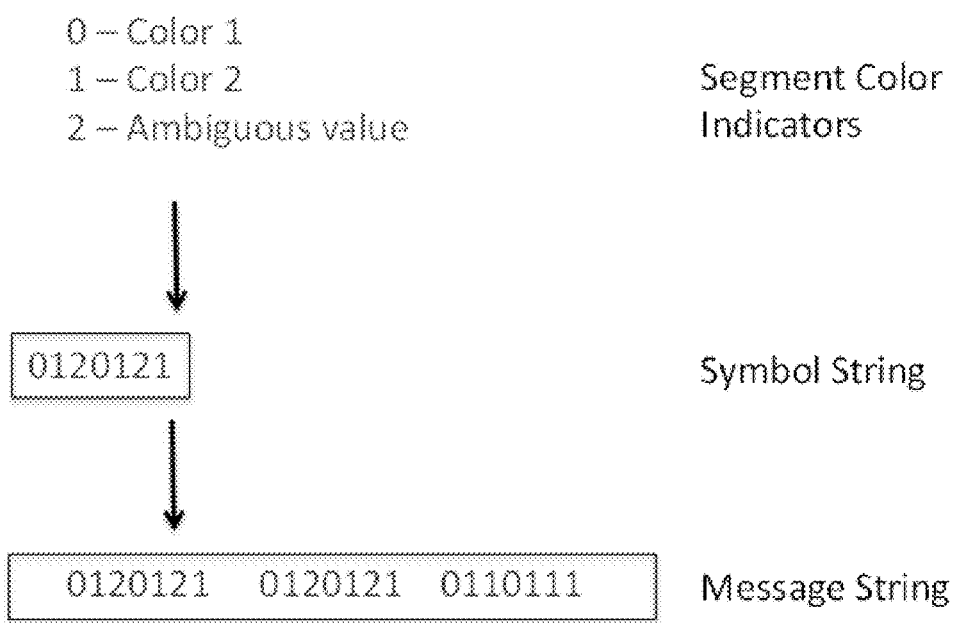
FIG. 17 is a diagram of color strings, segment strings and message strings in accordance with the present invention.
Figure 18:
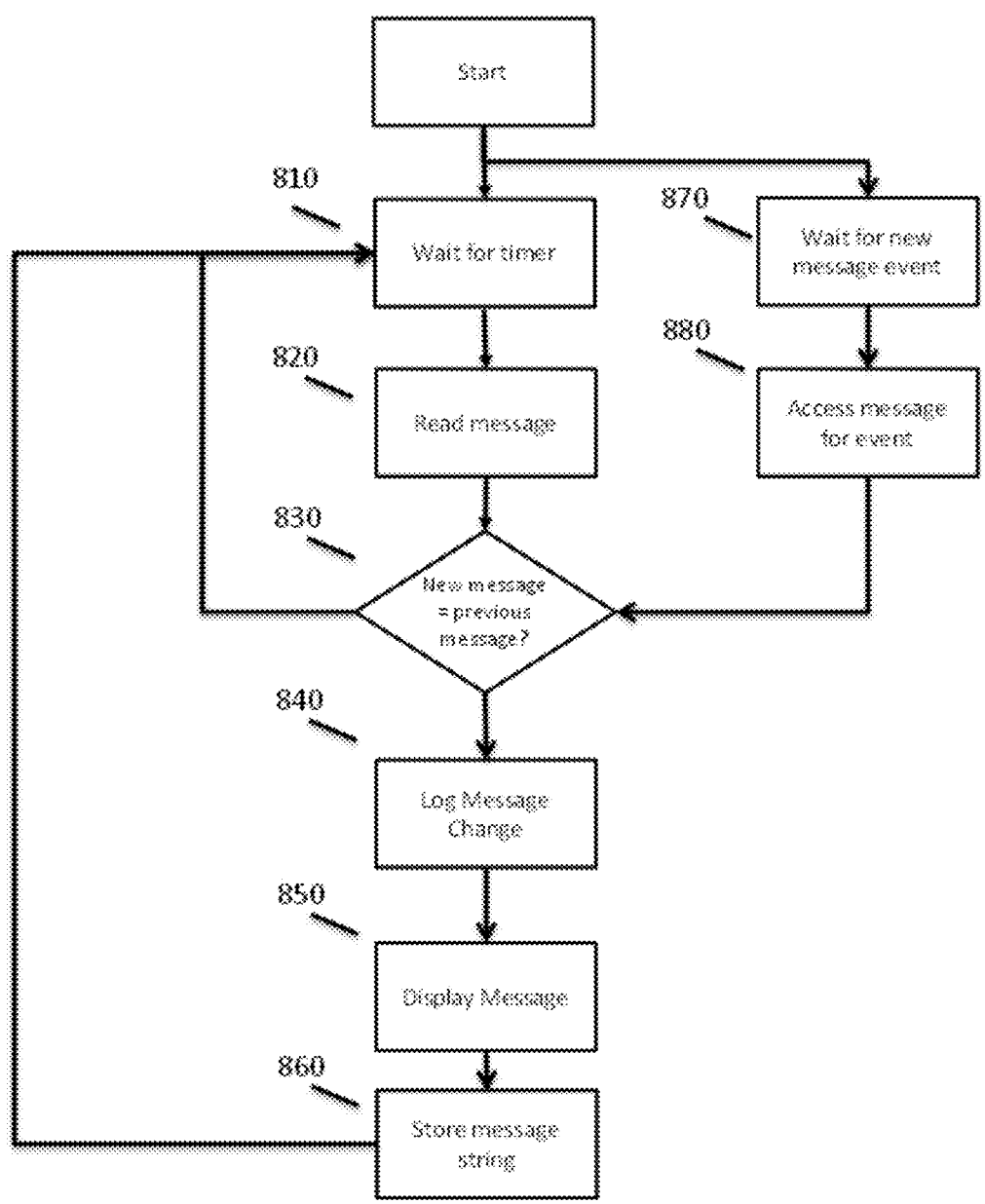
FIG. 18 is a diagram of the main message process in accordance with the present invention.

Process 700, Build Symbol Mask, is diagrammed in FIG. 16. Process 700 takes as input a Symbol String and builds a bit mask. This bit mask has a 1 for every segment that has an unambiguous read and a 0 for every segment in which the segment string value is ambiguous. Process 700 begins in process step 710 where the segment index (SI) is set to 1. Process 700 proceeds to process step 720 where the value of the Symbol String at the SI position is ambiguous. If the Symbol String at this position is ambiguous, Process 700 proceeds to process step 760 where the mask bit at position SI is set to 0. Process 700 then proceeds to process step 740. If in process step 720 the Symbol String at position SI was not ambiguous, process 700 proceeds to process step 730 where the Mask bit at position SI is set to 1. Process 700 then proceeds to process step 740 where the segment index is incremented. Process 700 then proceeds to process step 750. In process step 750 the SI is compared to the Symbol String length. If this was not the last symbol, Process 700 proceeds to process step 720. If it was the last segment in the Symbol String process 700 proceeds to process step 700 where the symbol mask is returned. Process 700 then terminates. FIG. 17 shows examples of color indicator values, a symbol string, and a message string.

Process 800, Message Processing, is an asynchronous process driven by a timer or external interrupt. Process 800 (FIG. 18) begins in process step 810 where it waits on a timer interrupt. Once the timer is triggered, Process 800 continues to process step 820 where process 400, Build Message String, is invoked. Process 800 then continues to process step 830 where the new message string is compared to the previous message string. If the new message string is equal to the previous message string, Process 800 proceeds to process step 810. If the new message string is not equal to the old message string, Process 800 continues to process step 840, where the changed message is logged.

The log entry for the message can include a date and timestamp, the message string, and other sensor information that may be both available and relevant (e.g., temperature) for the given device configuration and context. This log entry can be saved in local device memory, external storage device or can be transmitted to a remote site for storage and further processing.

Process 800 then continues to process step 850 where process 500, Display Message is invoked. Process 800 then continues to process step 860 where the current message string is saved as the reference message string for subsequent comparisons.

In process step 870 Process 800 waits for a new message event. This event is device dependent and may be triggered by local sensors or may be externally triggered for purposes of setting the display configuration. Once triggered, Process 800 continues to process step 880 where the message for the event is accessed. This access may be through a lookup table based on possible events, may be supplied by an external source, or may be constructed based upon multiple sources of information available to the device. Process 800 then continues to process step 830.

Electrophoretic Display with Electrically Determined Display State

Bistable electrophoretic displays typically employ an electric switching (or write) signal applied to a pair of addressing pixel electrodes that is characterized by a square pulse with specific voltage amplitude, polarity, and duration. The application of such a pulse forms an electric field within the compartments containing the ink particles and suspension fluid that causes the charged particles to migrate toward the walls of the compartment in, or in opposite, direction of the field depending of the charge of the particles. The migration speed of the particles is to first order proportional to the applied field, but may also be non-linear with respect to the applied field and exhibit a threshold in the electrical field, i.e., a minimum field required to cause migration, depending on the selection of the type of ink particle, its sticking properties to one another and the compartment wall, as well as, the rheology of the suspension fluid. With this in mind, the combination of voltage amplitude and duration of the switching signal is selected to achieve sufficient migration of the ink particles to achieve a well-defined state at which all, or substantial majority, of the particular type ink particles are settled at the containment (capsule) wall. During this migration of the charged ink particles, a transient current is induced characterized by a sharp rise to a peak followed by an exponential decline eventually reaching an approximately zero current or some steady low leakage current level.

The application of a single write pulse for electrophoretic displays can, however, also be broken in into a series of smaller effect pulses accumulatively achieving a similar switching effect. In this invention, the methods and systems of applying smaller effect pulses to determine the state of a pixel in an electrophoretic display are disclosed. Such smaller effect pulses, hereinafter referred to as perturbation pulses, have a smaller cumulative effect than that of a nominal write pulse required to reliably switch the pixel state of an electrophoretic display and preferably are of a magnitude as to not significantly change the display state or the displayed message. For example, the effect of the perturbation pulses would preferably not change the display state more than that associated with shorter term settling or longer term degradation of the display state, or such that the message on the display would be compromised.

The system for electrical display state determination comprises the following components:

a display medium, the display medium having at least one addressable display pixel capable of displaying at least two stable optical states, the display pixel having a first and a second addressable electrode, the first electrode being pixelated containing a pixel corresponding to the addressable display pixel;

a signal generator for applying at least a first electrical signal to the first electrode and a second electrical signal to the second electrode (a perturbation pulse);

a detection circuit for measuring at least an electrical characteristic of at least one the display pixels, the electrical characteristic generated in response to the applied first electrical signal and said second electrical signal; and a processor for determining the optical state of the display pixel from at least the detected electrical characteristic.

The above components can be integrated into a self-contained display/state determination system. However, depending on the complexity, the processor may preferably be external to the other components, with an added communication system (e.g., hardwired or wireless).

The signal generator produces the perturbation pulses, which may be selected to have the same nominal voltage amplitude as that of the write pulses of the display medium. However, a smaller or a higher amplitude may be selected with an appropriate selection of the pulse duration. The perturbation pulses may further have a multitude of amplitudes, arbitrary waveforms, durations, or AC components. The perturbation pulses may also be preconditioned by a series of AC pulses in order to overcome any significant sticking condition with the ink particles, to provide for more consistent or distinct current transients. Furthermore, the delay in-between consecutive pulses may be selected as appropriate with or without the application of a DC bias. It should also be noted that it is preferable to select the perturbation pulses such that the SNR of the induced transient currents are sufficient for reliably characterization, in particular, for cases in which the pixel areas or the quantity of charged ink particles within the pixel are small.

The application of the perturbation pulses can be to a set of electrodes configured around the each ink compartment (microcapsule), but favorably to a set of electrodes congruent with at least one pixel of the display. Even more preferable is to apply the perturbation pulses to the same set of electrodes used by the write signal, which may include a common electrode on one side of the display.

The perturbation pulses may be calibrated or compensated based on the temperature of the display, the size of the pixel, pixel to pixel variation, or pixel dependent stray capacitance. The temperature of the display may be determined by a separate sensor integral to the display, preferably near the display layer itself, or indirectly through a characteristic of the display (e.g., leakage current) which is coupled to the temperature behavior of the display. The calibration scheme may be based on self-calibration or by use of off-line external optical detection such as a spectrophotometer.

For each perturbation pulse, the induced transient current can be measured and its characteristics be determined in the detection circuit, e.g., using threshold detection. Such characteristics may include the peak current, average current, time to half peak current, or temporal integration of the current (charge). It may further be preferable to only determine its characteristics based on a portion of the transient current response (i.e., within a determination window). For instance, the determination window may be a certain fraction of the total transient duration aligned with the leading, the trailing, or some middle part of the transient duration. The induced transient current and its characteristic depends not only on the state of the display and the specifics of the applied perturbation pulse, but also on the detailed properties of its physical and electrochemical composition and resulting electrophoretic behavior, including but not limited to the choice of suspension fluid, selection of ink particle(s), additives such as surfactant (and resulting micelles), and degree of sticking of the ink particle(s) in the particular state of the display at which the perturbation pulse is applied. Based on a series of applied perturbation pulses, their polarities, and the pattern of their determined characteristics from their respective transient currents, the state of the pixel can be inferred and the functionality and integrity of the display pixel be assessed. A series of restoring perturbation pulses can optionally and subsequently be applied to reset the display pixel to its original state, or to the original intended state.

In order to further enhance the current transients resulting from the perturbation pulses, it may be desirable to optimize the mobility of the charged ink particles and associated micelles within the suspension fluid in the microcapsules, and to minimize any leakage currents. For instance, it may be desirable to enhance the current transients such that the distinct display states can more readily be differentiated. This may further be done within the constraints of available switching voltage amplitude and selected perturbation pulse duration in relation to the write pulse duration. For systems with more than one type of ink particle, it may be advantageous to independently optimize the mobilities of the several types of particles.

The detection of the induced transient currents by the perturbation pulses for reliable determination of the state of the display is impacted by systematic and random noise. It is therefore desirable to not only reduce electronics noise (e.g., employ common mode noise reduction techniques), but also to reduce variation induced by the electrophoretic display mechanism itself. For instance, it is desirable to control the size, symmetry, density, charge and distribution of the ink particles, the microcapsules (e.g. diameter and wall thickness), and any other layer/material in-between the electrodes of the display.

Exemplary Embodiments

Figure 19A:
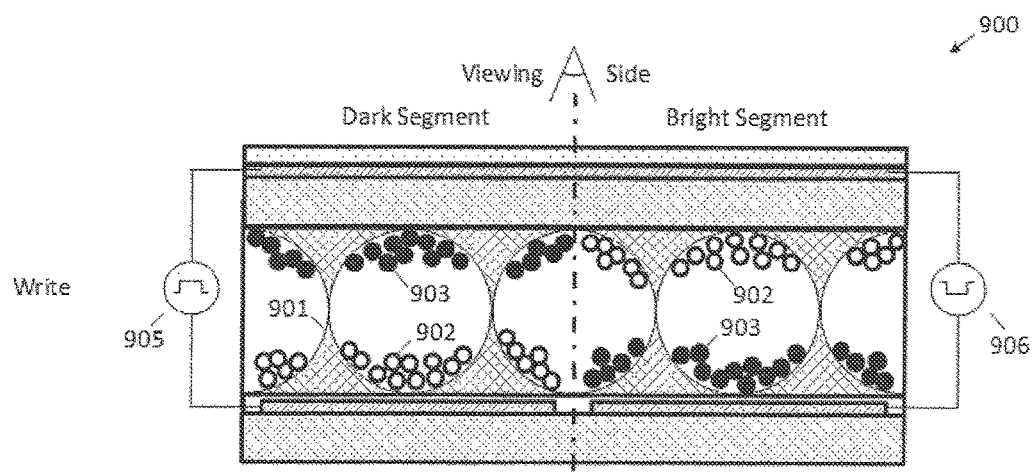
FIG. 19A and FIG. 19B are diagrams of an electrophoretic display in accordance with the present invention.

FIG. 19A illustrates a cross-section of a typical construction of an electrophoretic display 900 with microencapsulated 901 ink particles. In this example there are two types of ink particles contained within each capsule corresponding to two colors and two display states: a first color here generated by white ink particles 902 and here assumed to have a positive charge; and a second color here generated by black ink particles 903 and here assumed to have a negative charge. When subjecting the front and back electrodes to a potential difference 905 of some appropriate duration, the differently charged ink particles will move in opposite directions until all particles congregate at their respective side of the microcapsule. By switching the polarity 906 both optical display states (in this example dark and bright) can be achieved for each pixel/segment as shown in FIG. 19A. Both the voltage amplitude and the duration of the write pulse at a particular temperature determine the final state of display. It may be desirable not to apply a too large of a combination of voltage amplitude and duration of the write pulse as this may create an overdriven condition in which the first state cannot easily be reverted to the complementary second state, or vice versa. Once a display state has been achieved, and after some possible shorter term settling, it can remain stable for a significant amount of time. During this stable phase the display state can be electrically verified by subjecting it to a series of short bipolar pulses.

Figure 19B:
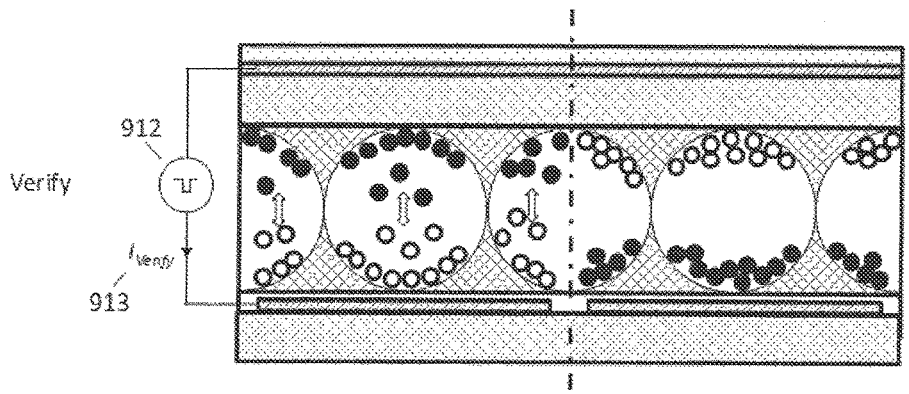

As illustrated in FIG. 19B, if the particular stable first state (in this example, dark) is subjected to a verification or "perturbation" pulse 912, which is of opposite polarity and a shorter duration to that of the typical write pulse (in FIG. 19A), some or all of the black and white ink particles will start to move toward their respective opposite side. During this process there will be a transient verification current, $I_{Verify}$ 913 present as indicated in FIG. 19B. This current can further be processed in order to extract an electrical or further logical verification signal reflecting the optical state of the pixel/segment of the display. For instance, its peak magnitude can be converted into a peak voltage level, or the transient current over an appropriate point of time can be integrated and provide a subsequent voltage level representative of the display state. Hereinafter $I_{Verify}$ will symbolically denote the response from the display pixel/segment when subjected to a verification pulse using any appropriate signal processing scheme. Based on the magnitude of $I_{Verify}$ in response to an initial pulse and possibly additional pulses, the optical state can be deduced to be in one of the following states: dark/black, intermediate/grey, and bright/white.

It should be noted that for this exemplary "bistable" configuration comprising the two optical states of a first state (here dark as seen from the viewing side when black ink particles are situated near the viewing side of the microcapsules) and a second state (here bright when white ink particles are situated by the viewing side), intermediary states corresponding to particular grey levels are also possible. The particular level of grey depends on the fraction of the black versus white ink particles are seen from the viewing side of the microcapsule(s) defining the pixel/segment.

Figure 20:
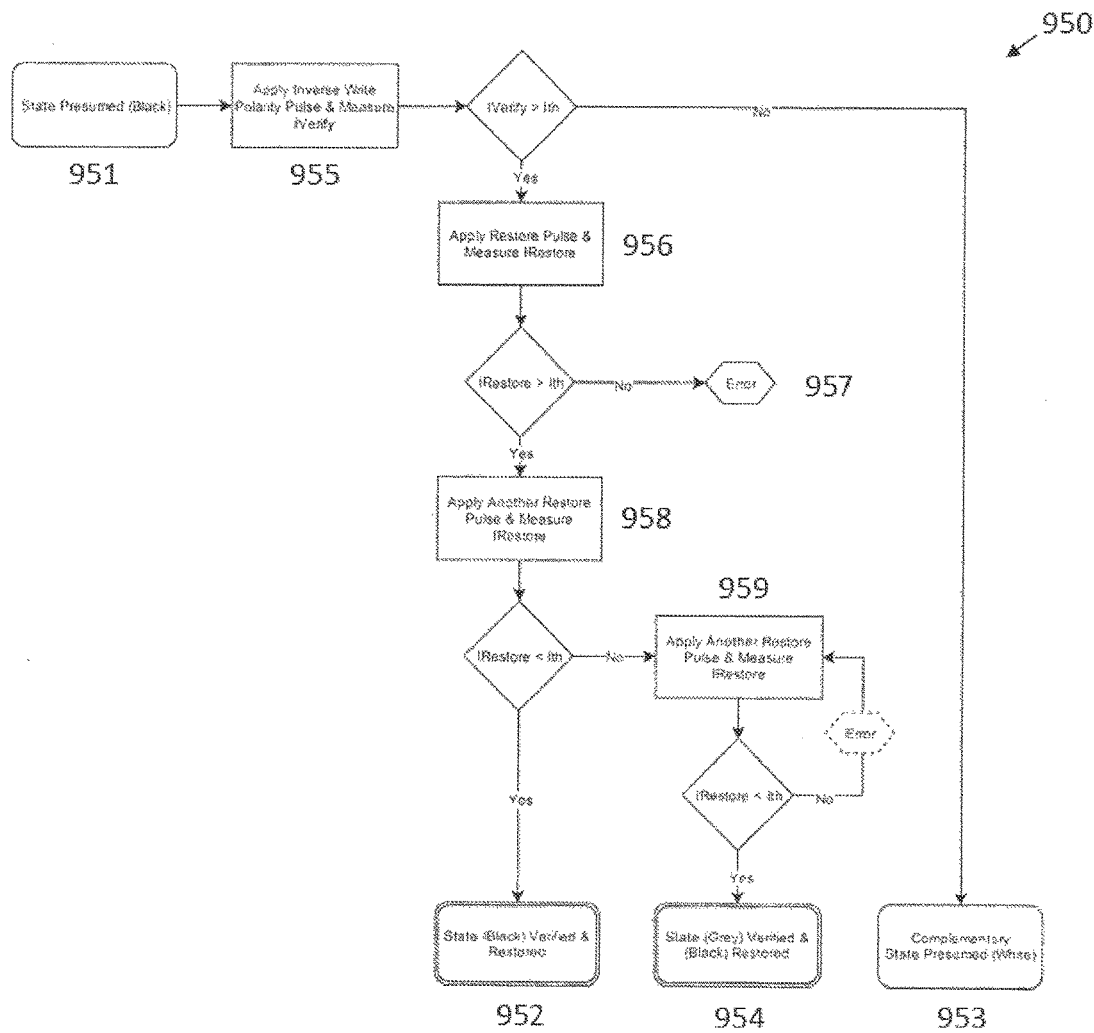
FIG. 20 is a flow chart for an exemplary display state verification process in accordance with the present invention.

FIG. 20 illustrates a flow diagram 950 for an exemplary display state verification process using this state perturbation approach. This flow diagram outlines process steps to determine the whether the present optical state 951 presumed to be of a first color (here black/dark) is indeed correct 952, or rather is presumed to be that of the second color (here white/bright) 953, or if the state is determined to be that of an intermediary color (here grey) 954. Firstly, a verification pulse of inverse polarity to that of write pulse for the presumed optical state is applied 955. If the resulting verification current, $I_{Verify}$, is lower (or equal) than a certain appropriate threshold, $I_{th}$, there is little or no movement of the ink particles indicating that the initially presumed optical state was incorrect, and rather now is presumed to be the complementary optical state (bright/white state) 953. In this case the process can be redone with the complementary state as the starting point to confirm this. As discussed above, a perturbation pulse of the same polarity as the write pulse of the presumed state 951 could be applied in this first step 955. However, for reasons mentioned above, a false positive verification of the state could result if the pixel/segment is not functioning normally.

Conversely, if $I_{verify}$ is larger than $I_{th}$, then some movement of ink particles have taken place and the pixel/segment is assumed to be functioning normally. However, it cannot be verified at this stage that the optical state is indeed corresponds to a first color (dark/black) or some intermediate grey color. In order to determine this, a restore pulse with comparable duration and amplitude but opposite polarity to that of the initial verification pulse is applied to the specific pixel/segment 956. This would allow the ink particles to approximately move back to that of the original state in 951, and further reconfirm the normal functionality of the pixel/segment, or else it would imply an erroneous behavior 957. If yet an additional restore pulse were applied 958 yielding a restore current (or signal) $I_{Restore}$ less than $I_{th}$, the original state has been restored and confirmed to be of a first color (dark/black) 952, or else additional restore pulse(s) can be applied 959 iteratively (for example, n-times, where n is an integer) implying an original intermediate/grey state with a restored state with a first color of dark/black 954. For cases in which the electrophoretic display exhibits longer term state instability (for instance, a black color state slowly degrading towards a grey intermediary level), this scheme provides for a state refreshing capability during the state verification process at appropriate time intervals.

Although the inventions disclosed herein are focused on bistable and multistable electrophoretic displays, the systems and methods and be extended to other bistable or multistable displays.

While particular preferred and alternative embodiments of the present intention have been disclosed, it will be appreciated that many various modifications and extensions of the above described technology may be implemented using the teaching of this invention. All such modifications and extensions are intended to be included within the true spirit and scope of the appended claims.

What is claimed is:

1. A verifiable display, comprising:
a set of display pixels, each pixel having at least two optical states and a first electrode and a second electrode, wherein the first and second electrodes are positioned adjacent the top and bottom of each respective pixel;
a first electrical signal generator coupled to the first electrode and the second electrode, the first signal generator generating a write signal that creates a first electrical differential between the electrodes to set a pixel into a desired optical state that changes the visible perceptibility of the pixel;
a second electrical signal generator coupled to the first electrode and the second electrode, the second signal generator generating a second electrical signal such that the application of the second signal across first and second the electrodes does not change the visible perceptibility of the pixel;
a detection circuit coupled to the first and second electrodes of the pixel for measuring an electrical response to the second electrical signal that correlates with the contrast level of the pixel; and
wherein the contrast level is used to evaluate the visible perceptibility of the pixel at the time the second electrical signal was applied.

2. The verifiable display of claim 1 wherein the first signal generator and the second electrical generator are the same.

3. The verifiable display of claim 1 wherein the pixels are electrophoretic.

4. The verifiable display of claim 1 wherein the signal generators are constructed to generate the write signal as a pulse and the second signal as a pulse shorter than the write signal pulse.

5. The verifiable display of claim 1 wherein the second electrical signal is selected to have a different electrical characteristic than the write first electrical signal.

6. The verifiable display of claim 5 wherein the electrical characteristic is amplitude, duration, voltage, or waveform shape.

7. The verifiable display of claim 1 wherein the second electrical signal generator is constructed to generate the second signal as a perturbation signal.

8. The verifiable display of claim 7 wherein the perturbation signal is of the opposite polarity as the write signal.

9. The verifiable display of claim 7 wherein the perturbation signal is a set of pulses.

10. The verifiable display of claim 1 wherein the detection circuit is constructed to measure current flow.

11. The verifiable display of claim 1 further comprising a processor constructed to compare the electrical response to a predetermined threshold to determine the optical state of the pixel.

12. The verifiable display of claim 1 further comprising an environmental sensor to detect an environmental condition, and the detected environmental condition is used to compensate the second electrical signal.

13. The verifiable display of claim 12, wherein the environmental sensor is a temperature sensor arranged to detect the temperature of the display, a temperature sensor arranged to detect the temperature of ambient air, a pressure sensor, or a humidity sensor.

14. A method for verifying a display, comprising:
providing a pixel for the display, the pixel having a pair of electrodes that receive a write signal;
presuming the pixel is in a first optical state of a plurality of possible optical states, the first optical state corresponding to a contrast level that provides an intended visible perceptibility;
setting a threshold value according to the contrast level for the presumed first optical state;
applying, using the pair of electrodes, a second signal to the pixel such that the second signal does not change to visible perceptibility of the pixel;
measuring an electrical response of the pixel to the second signal, the measured signal correlating to the actual contrast level of the pixel;
comparing the contrast level for the measured electrical response to the contrast level for the threshold value; and
determining, using the comparison, whether or not the pixel is in the presumed optical state such that the pixel has the contrast level to provide the intended visible perceptibility.

15. The method according to claim 14, further including the step of applying a restore signal to the pixel after the electrical response has been measured.

16. The method according to claim 14, further including the steps of:
applying a write signal to the pixel at a polarity to set the pixel into the presumed optical state;
using the measured signal to generate a restore threshold;
applying a restore signal at the same polarity as the write signal to the pixel after the electrical response has been measured;
measuring an electrical restore response of the pixel to the restore signal;
comparing the measured restore response to the restore threshold value to determine which of the plurality of possible optical states the pixel is actually in.

17. The method according to claim 14, further including the step of applying the second signal as a perturbation signal.

18. The method according to claim 17, further including the steps of:
applying a write signal to the pixel at a polarity to set the pixel into the presumed optical state; and
applying the perturbation signal at the opposite polarity.

19. The method according to claim 17, wherein the step of applying the perturbation signal comprises applying a series of pulses.

20. The method according to claim 17, wherein the step of applying the perturbation signal comprises setting the perturbation signal to be at an amplitude smaller than the amplitude of the write signal.

21. The method according to claim 17, wherein the step of applying the perturbation signal comprises setting the perturbation signal to be at a voltage different than the voltage of the write signal.

22. The method according to claim 17, wherein the step of applying the perturbation signal comprises setting the perturbation signal to be at shorter duration than the duration of the write signal.

23. The method according to claim 17, wherein the step of applying the perturbation signal comprises setting the perturbation signal to be a different waveform than the waveform of the write signal.

24. The method according to claim 17, wherein the step of applying the perturbation signal wherein the time integral of the amplitude of the perturbation signal is smaller than the time integral of the amplitude of the write signal.

25. The verifiable display of claim 14 wherein the second signal is selected to have a different electrical characteristic than the write electrical signal.

26. The verifiable display of claim 25 wherein the electrical characteristic is amplitude, duration, voltage, or waveform shape.

27. The method according to claim 14, further including the steps of:
applying, using the pair of electrodes, a plurality of second electrical signals to the pixel such that the plurality of signals does not change to visible perceptibility of the pixel;
measuring the electrical responses of the pixel to the plurality of the second electrical signals, the measured electrical responses used to determine the actual contrast level of the pixel;
comparing the contrast level for the measured electrical responses to the contrast level for the threshold value; and
determining, using the comparison, whether or not the pixel is in the presumed optical state such that the pixel has the contrast level to provide the intended visible perceptibility.

28. A method for verifying a display, comprising:
providing a pixel in an optical state that has a visible perceptibility;
applying a perturbation signal to the pixel that does not change the visible perceptibility of the pixel, the perturbation signal being applied to the pixel using the same electrodes used to set the pixel into a desired optical state;
measuring an electrical response of the pixel to the perturbation signal; and
determining, using the measured value, the optical state of the pixel at the time the perturbation signal was applied.

29. The method according to claim 28, wherein the determining step comprises comparing the measured value against predetermined values.

30. The method according to claim 28, wherein the determining step comprises comparing the measured value against values in a look-up table.

31. An intelligent label, comprising:
a processor;
an electrophoretic display comprising a plurality of pixels;
a power source;
wherein the processor operates a method comprising:
applying a perturbation signal to one of the pixels that does not change the visible perceptibility of the pixel;
measuring an electrical response of the pixel to the perturbation signal; and
determining, using the measured value, the optical state of the pixel at the time the perturbation signal was applied.

32. The intelligent label according to claim 31, wherein, prior to applying the perturbation signal, the processor further operates the step of applying a write signal to the pixel to set the pixel in a presumed optical state.

33. The intelligent label according to claim 31, further comprising:
an environmental sensor to sense an environmental condition; and
wherein the perturbation signal is set, calibrated or adjusted responsive to the environmental condition.

34. The intelligent label according to claim 31, wherein the perturbation signal is applied responsive to time or an elapsed time.

35. The intelligent label according to claim 31, further comprising:
a communication circuit for receiving a message; and
wherein the perturbation signal is applied responsive to the message.

36. A verifiable display, comprising:
a set of display pixels, at least one of the pixels having an electrode pair, the electrode pair arranged to set the pixel into an optical state with a level of visible perceptibility;
an electrical signal generator coupled to the electrode pair, the signal generator constructed to apply a verification signal at the electrode pixels that does not change visible perceptibility of the pixel;
a detection circuit coupled to the electrode pair for measuring an electrical response to the second signal; and
wherein the measured electrical response is correlated to the visible perceptibility of the pixel at the time the verification signal was applied to the electrode pair.

37. The verifiable display according to claim 36, wherein the signal generator is further constructed to apply a write signal at the electrode pair to set the pixel into a desired optical state.

* * * * *